United States Patent
Buck

[11] 3,975,422
[45] Aug. 17, 1976

[54] PREPARATION OF BIS (2-CYANOACRYLATE)MONOMERS

[75] Inventor: Carl J. Buck, Berkeley Heights, N.J.

[73] Assignee: Johnson & Johnson, New Brunswick, N.J.

[22] Filed: Oct. 4, 1974

[21] Appl. No.: 512,276

Related U.S. Application Data

[63] Continuation-in-part of Ser. No. 308,375, Nov. 21, 1972, abandoned, and Ser. No. 308,376, Nov. 21, 1972, abandoned.

[52] U.S. Cl. .............................. 260/465.4; 260/42; 260/42.18; 260/46.5 UA; 260/47 UA; 260/79.7; 260/448.2 N; 260/464; 260/465 D; 526/298
[51] Int. Cl.² .................................. C07C 120/00
[58] Field of Search ............. 260/465.4, 465 D, 464, 260/448.2 N

[56] References Cited
UNITED STATES PATENTS

| | | | |
|---|---|---|---|
| 3,142,698 | 7/1964 | Halpern et al. | 260/465.4 |
| 3,463,804 | 8/1969 | Ray et al. | 260/465 D |
| 3,616,269 | 10/1971 | Aelony et al. | 260/465.8 X |
| 3,655,721 | 4/1972 | Arni et al. | 260/465.8 R |
| 3,853,945 | 12/1974 | Weiss et al. | 260/465.4 |

*Primary Examiner*—Joseph Paul Brust

[57] ABSTRACT

Difunctional monomers of the formula,

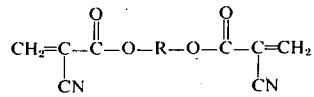

where R is an organic linking group derived from a diol or a dihalide of the formula X-R-X, where X is either chlorine, bromine, iodine, or hydroxy, are prepared by reacting a conjugated diene, exemplified by anthracene, with an ester of 2-cyanoacrylic acid to form the Diels-Alder adduct of the ester. The ester adduct is hydrolyzed to ultimately obtain either the Diels-Alder adduct of either 2-cyanoacrylic acid--alkali metal salt or 2-cyanoacryloyl halide. These latter intermediates are respectively reacted with either the dihalide or the diol to afford the bis-Diels-Alder adduct of the R substituted bis (2-cyanoacrylate) monomer. The protective diene group may then be removed, for example, by reaction with excess maleic anhydride and the resulting difunctional monomer isolated.

The difunctional monomers thus prepared can be utilized as crosslinking agents in blends comprising one or more of these difunctional monomers and at least one monofunctional monomer, exemplified by an ester of 2-cyanoacrylic acid. Alternately, one or more difunctional monomers can be homopolymerized or copolymerized to a highly crosslinked polymer. The copolymerized compositions of the monomer blends are particularly useful as adhesives, especially in dental applications for coating or sealing enamel surfaces of teeth to allay decay, or for the bonding of brackets to teeth in orthodontics the bond being substantially more resistant to moisture than where the monofunctional monomer is used alone.

17 Claims, No Drawings

PREPARATION OF BIS (2-CYANOACRYLATE)MONOMERS

This application is a continuation-in-part of copending applications Ser. No. 308,375 filed Nov. 21, 1972, and Ser. No. 308,376, filed Nov. 21, 1972, both now abandoned.

DISCLOSURE OF THE INVENTION

1. Field of the Invention

This invention relates to new and novel compositions and to methods for preparing the same. In particular, this invention relates to methods for preparing new bis esters represented by

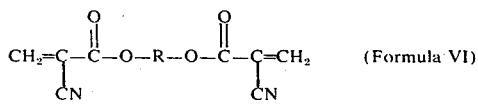
(Formula VI)

of the following "Flow Chart" and

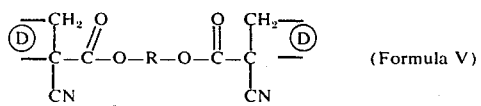
(Formula V)

where R is an organo linking group and ⒹΞ is a blocking group derived from a cyclic 1,3 diene. The monomers represented by formula I prepared by this process have been found to be particularly useful as adhesives, especially in dental applications when incorporated as crosslinking agents for esters of 2-cyanoacrylic acid. The bis esters represented by Formula V are particularly useful in the preparation of monomers of Formula VI.

2. Description of the Prior Art

The production of esters of 2-cyanoacrylic acid via in situ formation of the Diels-Alder anthracene adducts of 2-cyanoacrylic acid esters is described in U.S. Pat. No. 3,463,804. This patent, however, is concerned only with the preparation of the monofunctional monomers, such as the esters of 2-cyanoacrylic acid, and makes no reference to any means for obtaining a difunctional bis (2-cyanoacrylate) ester, such as of this invention, which can be polymerized alone, or in admixture with other 2-cyanoacrylate esters or bis (2-cyanoacrylate) esters, to afford crosslinked polymeric compositions. Japanese Patent 46-5135 (1971) discloses a similar process and likewise makes no reference to bis (2-cyanoacrylate) monomers.

U.S. Pat. No. 3,142,698 purports to disclose a method of preparing various difunctional monomers, including some of this invention. The method disclosed in U.S. Pat. No. 3,142,698 entails the preparaton of an alkylene glycol dicyanoacetate from an alkylene glycol and cyanoacetic acid. The alkylene glycol dicyanoacetate is then condensed with formaldehyde to allegedly produce the alkylene glycol bis (2-cyanoacrylate). All attempts to produce such difunctional monomers in accordance with the teachings of that disclosure have proven completely unsuccessful. The products obtained are polymeric and, unlike the difunctional monomers of this invention, are insoluble in most common organic solvents such as chloroform, benzene, acetone, and the like. Infrared analysis (IR) of the resinous product confirmed the absence of any monomer having the alleged structure and, instead, showed a product having strong residual hydroxyl group absorptions. The IR data, coupled with the insolubility of the product, suggests that the formaldehyde has reacted with the alkylene glycol dicyanoacetate in an adverse manner so as to give a highly crosslinked polymeric composition instead of the alleged monomeric structures.

Efforts to develop difunctional monomers bearing the highly reactive cyanoacrylate functional group and which can be employed as a crosslinking agent with other monofunctional monomers that polymerize through a vinyl bond, particularly the cyanoacrylates, have heretofore been without actual success.

Therefore, the primary object of this invention is to provide a method for preparing bis (2-cyanoacrylate) monomers and to provide compounds that can readily be converted to bis (2-cyanoacrylate) monomers so that the same can be employed as crosslinking agents, particularly for monofunctional esters of 2-cyanoacrylic acid.

A further object of this invention is to provide crosslinkable adhesive compositions comprising 2-cyanoacrylate esters and difunctional bis (2-cyanoacrylate) monomers which, upon copolymerization form a crosslinked polymer having improved resistance to moisture and improved adhesive and cohesive bond strength over that obtainable through the use of the cyanoacrylate ester alone.

Another object of this invention is to provide compositions for performing dental prophylaxis, for preparing dental restorations, or for bonding dental devices to teeth, such compositions having improved adhesion to tooth structure as well as improved strength properties.

It is a still further object of this invention to provide a composition for use as a pit and fissure sealant that has improved adhesive and cohesive strength to enable it to better withstand the grinding forces which teeth undergo.

SUMMARY OF THE INVENTION

These and other objects and advantages are achieved by preparing the bis (2-cyanoacrylate) monomers of this invention in accordance with the general reaction scheme set forth below. In this scheme the active vinyl group,

of a 2-cyanoacrylate ester (Formula I of Flow Chart) is first blocked by adding a blocking group, designated by

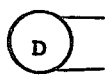

through a conventional Diels-Alder rection which blocking group is maintained until the bis acrylate is formed. The blocking group

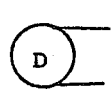

is then removed, restoring the active vinyl groups of the bis 2-cyanoacrylate. This is illustrated in the following Flow Chart to which reference is now made. Referring to the following Flow Chart, an ester of 2-cyanoacrylic acid of General Formula I is reacted with a cyclic 1,3-diene to form a Diels-Alder adduct represented by General Formula (II). Typically, where anthracene is employed as the 1,3 diene and isobutyl 2-cyanoacrylate as the ester of Formula I, the Diels-Alder adduct of Formula II would be 11-cyano-11-carboisobutoxy-9,10-dihydro-9,10-endoethanoanthracene represented as

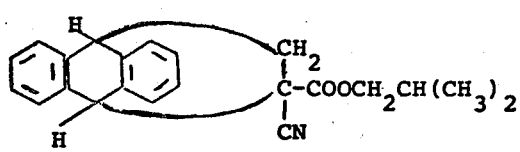

The adduct of General Formula II in which

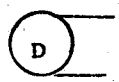

is the anthracene blocking group is then subjected to alkaline hydrolysis followed by acidification to form the corresponding 2-cyanoacrylic acid adduct represented by Formula III. Treatment with alkali forms the alkali metal salt represented by Formula (IV-A). Alternatively, the 2-cyanoacrylic acid adduct of Formula (III) can be suitably converted to the 2-cyanoacryloyl halide adduct represented by the Formula (IV-B).

The metal salt of the 2-cyanoacrylic acid adduct of Formula (IV-A) is then reacted with a dihalide, X-R-X, where X is independently bromide, iodine, or chlorine in one approach or, in the other aproach, the 2-cyanoacryloyl halide adduct of Formula (IV-B) is reacted with a diol of the Formula, HO-R-OH. R, in each case is an organo linking group defined in more detail below. Either of these routes result in the formation of the bis-Diels-Alder adduct represented by Formula (V). This bis-Diels-Alder adduct may then be converted into its corresponding bis (2-cyanoacrylate) monomer, as represented by Formula (VI) by heating the adduct in the presence of excess maleic anhydride. In this reaction scheme,

represents the cyclic 1,3-diene blocking group inserted in the first step of the sequence via Diels-Alder adduct formation.

FLOW CHART

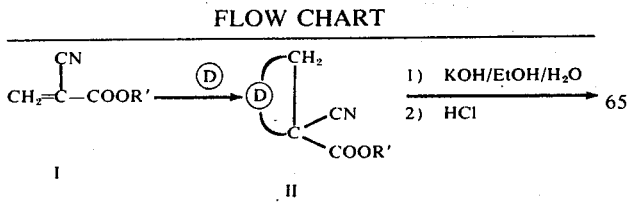

FLOW CHART-continued

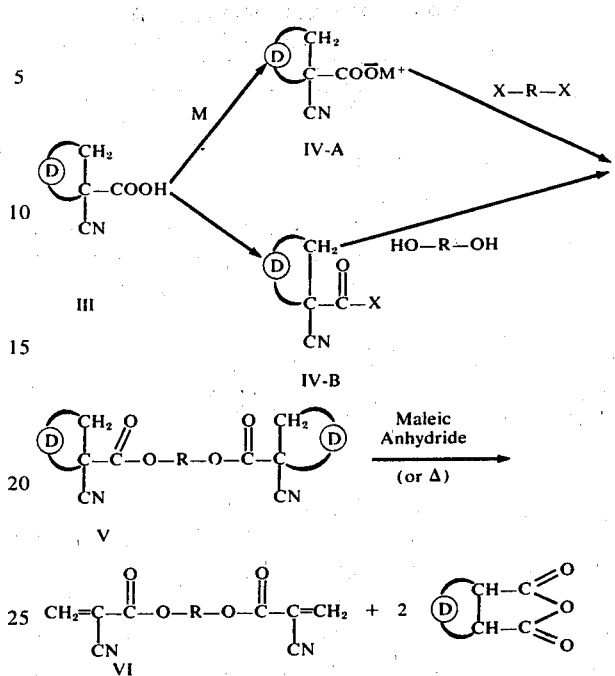

The monomeric esters (I) of 2-cyanoacrylic acid are well known and are described in U.S. Pat. No. 2,794,788. Since the ester group is subsequently hydrolyzed, the identity of the R' group of Formula I of the Flow Chart is immaterial. Therefore, R' can be $C_1$ to $C_{16}$ alkyl, cyclohexyl or phenyl. For convenience, isobutyl 2-cyanoacrylate is the preferred ester, R' being isobutyl. In the above scheme, it should also be noted that M denotes a monovalent, divalent or trivalent ion derived from a metal hydride, hydroxide, carbonate, alkoxide, or an organometallic agent.

Although the anthracene radical is preferred, in which case would be

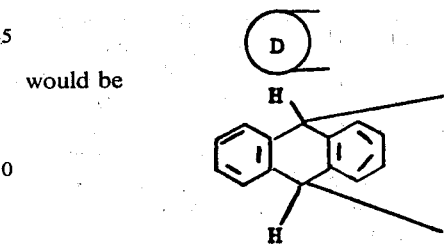

the 1,3-diene used to take part in the Diels-Alder adduct formation may be selected from a large number of compounds with the adducted 1,3-diene radical as represented by

being any of the radicals

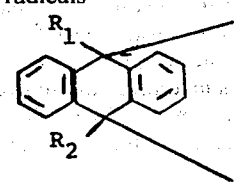

where $R_1$ and $R_2$ are the same $R_1$ and $R_2$ may be H, an alkyl group of 1 to 5 carbons, phenyl, Br or Cl. Where $R_1$ and $R_2$ are different, $R_1$ is H and $R_2$ may be any of the group consisting of an alkyl group of 1 to 5 carbons, phenyl, Br and Cl.

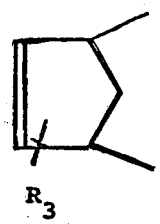

where $R_3$ is H or $CH_3$ and

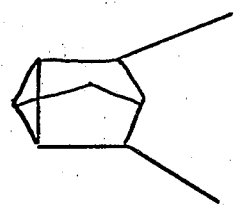

The organo linking group "R" appearing in the formulas of the above Flow Chart may be any of the group consisting of $$-(CH_2)_m-,$$

where $m$ is an integer of from 1 to 20 inclusive;

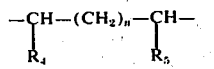

where $n$ is an integer of from 0 to 18 inclusive, and $R_4$ and $R_5$ are independently hydrogen or a $C_1$ to $C_5$ alkyl group, $R_4$ and $R_5$ not simultaneously being hydrogen;

$$-(CH_2)_r-Z-(CH_2)_s-,$$

where Z is $-O-$, $-S-$, $-CH=CH-$, $-C\equiv C-$,

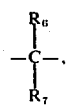

and

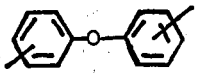

where $r$ and $s$ are independent integers of from 1 to 10 inclusive and $r$ and $s$ total from 2 to 20, $R_6$ and $R_7$ are independently hydrogen or a straight or branched chain $C_1$ to $C_5$ alkyl group;

where $x$ and $y$ are integers of from 1 to 6 inclusive;

where $x$ and $y$ are as hereinbefore defined;

$$-CH_2-(CF_2)_z-CH_2-,$$

where $z$ is an integer of from 1 to 10 inclusive; and

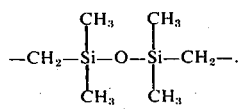

and wherein R' of Formula II is an alcohol moiety selected from $C_1$ to $C_{16}$ alkyl, cyclohexyl or phenyl.

One of the advantages of the process, as set forth in the above Flow Chart, is that it uses conventional reactions known to skilled chemists. These reactions, however, have been utilized in a new and novel sequence to produce highly useful bis cyanoacrylate products which previously could not be made.

Thus, the basic Diels-Alder reaction, going from Formula I to Formula II, is a well known type of reaction known and used by skilled chemists as is the saponification reaction followed by acidification used in going from the compound of Formula II to that of Formula III. However, compounds of the General Formula III were not known prior to my preparation and discovery thereof and form a critical step in the overall process described.

In like manner the metal salt-halide basic reaction is well known for linking together two acyl groups (the route through IV-A) as is the other route, that through IV-B wherein the carboxylic acid group is first converted to the acid halide and then esterified through reaction with a dihydroxy compound.

DETAILED DESCRIPTION OF THE INVENTION

Preparaton of the Diels-Alder Adducts of 2-Cyanoacrylic Acid Esters of 2-Cyanoacrylic Acid The difunctional monomers are prepared according to the method of this invention by the reaction of an ester of 2-cyanoacrylic acid (I) with a 1,3-diene to form the intermediate Diels-Alder adduct (II). This reaction is suitably carried out in an inert solvent such as, for example, benzene, toluene, or xylene or mixtures thereof. The reaction temperature can be anywhere from 5°C to the reflux temperature of the solution, depending on whether the reaction is exothermic or endothermic. The reaction is preferably carried out at the reflux temperature in benzene as solvent or, where the reaction is exothermic, at the ambient reaction temperature or at room temperature and below. Suitable dienes include those which will undergo 1,4-cycloaddition with a dienophile and which addition can be reversed after formation of the monomer adduct (V), such as, for example, by the application of heat or the addition of a more reactive dienophile such as maleic anhydride.

In this regard, cyclic 1,3-dienes are much preferred over the acyclic dienes (e.g., butadiene, isoprene, 1,3-pentadiene), since they afford Diels-Alder adducts with endo-bridges and which are more prone towards subsequent removal of the protective 1,3-diene moiety via a retrograde-diene scission. The bis-isoprene adduct intermediate corresponding to adduct V, for example, is highly resistant towards reverse Diels-Alder reaction, either thermally or by reaction with excess maleic anhydride. Typical examples of suitable cyclic 1,3-dienes are anthracene, the 9-substituted and 9,10-disubstituted anthracenes (9-methylanthracene, 9-bromoanthracene, 9-phenylanthracene; 9,10-dimethyl,- dibromo-, and -diphenylanthracenes), cyclopentadiene, methylcyclopentadiene, and norbornadiene. Preferred dienes from an availability standpoint, ease of adduct formation and subsequent retrograde-diene scission to the difunctional monomer (VI) in good yields and purity are anthracene, the 9-monosubstituted anthracene and 9,10-disubstituted anthracenes, and cyclopentadiene.

The preferred dieneophile is isobutyl 2-cyanoacrylate, and the reaction of this latter cyanoacrylate with anthracene will yield the anthracene/isobutyl 2-cyanoacrylate adduct (II) in nearly quantitative yield.

The 1,3-diene/alkyl 2-cyanoacrylate adduct (II) is then subjected to hydrolysis, preferably alkaline hydrolysis, to form the corresponding adduct of 2-cyanoacrylic acid (III). The hydrolysis is generally carried out in an aqueous alcoholic solution comprising the adduct of the ester of 2-cyanoacrylic acid (II) and an alkali metal hydroxide, and the solution is heated until the hydrolysis has been accomplished. The reaction is complete after one to five hours at reflux, but it is preferred to effect alkaline hydrolysis in as short a time as possible, preferably within one to two hours, to minimize or preclude concomitant hydrolysis of the cyano functional group. The hydrolyzed adduct is then acidified with hydrochloric acid, for example, to a pH of 2 and the crystalline Diels-Alder adduct (III) of 2-cyanoacrylic acid collected, washed with water, and dried.

Preparation of the Diels-Alder Adducts of 2-Cyanoacrylic Acid - Metal Salts and 2-Cyanoacryloyl Halides The 2-cyanoacrylic acid adduct (III) is then converted to either the 2-cyanoacryloyl halide adduct (IV-B) or the 2-cyanoacrylic acid - metal salt adduct (IV-A).

The 2-cyanoacrylic acid - metal salt adduct (IV-A) is suitably prepared by neutralizing an alcohol or acetone solution of the 2-cyanoacrylic acid adduct (III) with an alcoholic solution of an alkali metal hydroxide. Generally, the alcoholic solution of the alkali metal hydroxide is added dropwise to the solution of the acid adduct (III) until the pH is about 9.0, which pH has been determined to be the equivalence point. Preferred alkali metal hydroxides are sodium hydroxide and potassium hydroxide.

Alternate methods for preparation of the alkali metal salt adducts (IV-A) include the addition of stoichiometric quantities of alkali metal hydrides, preferably sodium hydride; alkali metal alkoxides, preferably sodium methoxide, sodium ethoxide, and potassium t-butoxide; alkali metal carbonates such as sodium carbonate and potassium carbonate; and organo lithium compounds such as butyl lithium and the like to the solution or suspension of the 2-cyanoacrylic acid adduct (Formula III).

The preferred metal salts of the 2-cyanoacrylic acid adduct (III) are those of the alkali metals in Group I of the Periodic Table, preferably sodium, potassium, and lithium. Adduct-metal salts (IV-A) of certain of the Group II elements, exemplified by magnesium, calcium, zinc, and barium, and trivalent metals from Group III, such as aluminum, can also be prepared from the requisite metal oxides, metal hydroxides, and metal carbonates.

The 2-cyanoacryloyl halides (IV-B) are prepared by reaction of the 2-cyanoacrylic acid adduct (III) with the halide reactant, preferably thionyl chloride or thionyl bromide, under anhydrous conditions in a suitable dry solvent, e.g., benzene, and in an inert atmosphere. While only a small excess of the thionyl halide reactant is required, a 25–200% excess is preferably employed. Alternately, a still larger excess of the thionyl halide can be utilized to function as both the solvent and reactant. Reaction is enhanced by employing a very small amount of either pyridine or N,N-dimethylformamide (DMF) as accelerators. The reaction is effected in an inert atmosphere at temperatures ranging from 5°C to 80°C and for about one to four hours, or until reaction is completed, as indicated by cessation of the evolution of hydrogen chloride and sulfur dioxide. Acid halide adduct (IV-B) is isolated by distillation in vacuo to remove any solvent and unreacted thionyl halide and purified by recrystallization from an inert solvent or, if sufficiently volatile, distillation under reduced pressure. A synthesis of the anthracene/2-cyanoacryloyl chloride adduct is exemplified in Example VI.

The 2-cyanoacryloyl halide adduct (IV-B) can also be prepared by utilizing reacants such as phosphorus trichloride and phosphorus pentachloride, whose use is well known to those skilled in the art.

After formation of either the adduct of 2-cyanoacrylic acid alkali metal salt (IV-A), or of the adduct of 2-cyanoacryloyl halide (IV-B), these respective intermediates are employed by respective reaction with a dihalide or diol to form the bis-Diels-Alder adduct of the bis (2-cyanoacrylate) monomer (V).

Preparation of the Bis-Diels Alder Adducts (V) of Bis (2-Cyanoacrylate) Monomers In general, about two moles of the Diels-Alder adduct (IV-A or IV-B) are employed for each mole of dihalide or diol reactant. Suitable dihalide or diol reactants include organic compounds having two reactive halogen or hydroxy substituents thereon, the dihalide of which will undergo a displacement reaction with the carboxylate salt and the diols of which undergoes an acrylation reaction with the 2-cyanoacryloyl halide to form the bis-Diels-Alder adducts (V) of the bis (2-cyanoacrylate) monomers. Examples of such compounds, wherein X is either independently selected from the halogens chlorine, bromine, iodine, or from hydroxy, include:

A. $X-(CH_2)_m-X$, where $m$ is an integer of from 1 to 20 inclusive, such as methylene iodide, 1,3-dibromopropane, 1,9-dibromononane, 1,12-dibromododecane, 1,3-propanediol, 1,9-nonanediol, and 1,12-dodecanediol.

B) 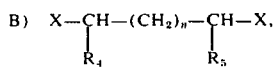

where $n$ is an integer of from 0 to 18 and $R_4$ and $R_5$ are independently selected from the group consisting of hydrogen and $C_1$ to $C_5$ alkyl, but $R_4$ and $R_5$ not simultaneously being hydrogen; such as 1,3-dibromobutane, 2,5-dibromohexane, 1,3-butanediol, and 2,5-hexanediol.

C. $X-(CH_2)_r-Z-(CH_2)_s-X$, where Z is $-O-$, $-S-$, $-CH=CH-$, $-C\equiv C-$,

and

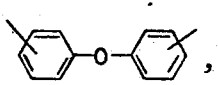

where $r$ and $s$ are independent integers of from 1 to 10 inclusive and $r$ and $s$ total from 2 to 20, $R_6$ and $R_7$ being as heretofore defined. The substitution on the aromatic ring is meta, para, or ortho; meta or para being preferred. The hydrogen atoms of the vinyl substituent are either cis or trans. Examples include: 2-chloroethyl ether, diethylene glycol, 4-chlorobutyl ether, 4-hydroxybutyl ether, 2-chloroethyl sulfide, 2-hydroxyethyl sulfide, 3-chloropropyl sulfide, 3-hydroxypropyl sulfide, trans-1,4-dibromo-2-butene, trans-2-butene-1,4-diol, trans-1,8-dichloro-4-octene, trans-4-octene-1,8-diol, trans-1,12-dichloro-6-dodecene, trans-6-dodecene-1,12-diol, 1,4-dichloro-2-butyne, 2-butyne-1,4-diol, 1,8-dichloro-4-octyne, 4-octyne-1,8-diol, 1,12-dichloro-6-dodecyne, 6-dodecyne-1,12-diol, 1,3-dibromo-2,2-dimethylpropane, -dihydroxy-1,3-dihydoxy-2,2-dimethylpropane, 4,4'-bis (chloromethyl) diphenyl ether, 4,4'-bis (hydroxymethyl) diphenyl ether and neopentyl glycol.

D. Alkylene glycols of the formula $HO[R''O]_tH$, where when $t$ is $\geq 1$, R'' is propylene, and when $t$ is $> 2$, R'' is also 1,4-tetramethylene and ethylene. The polyalkylene glycols are suitable in the higher molecular weight ranges generally to about a molecular weight of about 2000. Examples include propylene glycol, dipropylene glycol, polypropylene glycol, triethylene glycol, tetraethylene glycol, polyethylene glycol, and poly (1,4-tetramethylene glycol).

E.

where the substitution on the aromatic ring is meta, para, or ortho, and $x$ and $y$ are integers of from 1 to 6 inclusive such as 1,4-bis(chloromethyl) benzene, 1,4-bis(hydroxymethyl) benzene, 1,4-bis(4-bromobutyl) benzene, 1,4-bis(4-hydroxybutyl) benzene, 1-chloromethyl-4-(4-chlorobutyl) benzene and 1-hydroxymethyl-4-(4-hydroxybutyl) benzene.

F.

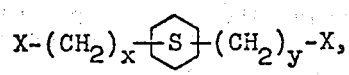

where $x$ and $y$ are as hereinbefore defined and the substitution on the cyclohexane ring is 1,2; 1,3; or 1,4 such as 1,4-bis(chloromethyl)cyclohexane, 1,4-bis(hydroxymethyl)cyclohexane, 1,4-bis(4-bromobutyl)cyclohexane, 1,4-bis(4-hydroxybutyl) cyclohexane, 1-chloromethyl-4-(4-chlorobutyl)cyclohexane, and 1-hydroxymethyl-4-(4-hydroxybutyl) cyclohexane.

G. $X-CH_2-(CF_2)_z-CH_2-X$, where z is an integer of from 1 to 10 inclusive such as 1,5-dibromo-2,2,3,3,4,4-hexafluoropentane, 1,5-dihydroxy-2,2,3,3,4,4-hexafluoropentane, 1,10-dibromo-2,2,3,3,4,4,5,5,6,6,7,7,8,8,9,9-hexadecafluorodecane, and 1,10-dihydroxy-2,2,3,3,4,4,5,5,6,6,7,7,8,8,9,9-hexadecafluorodecane.

H. $X-CH_2-Si(CH_3)_2-O-Si(CH_3)_2-CH_2-X$ such as 1,3-bis(chloromethyl)tetramethyldisiloxane or 1,3-bis(hydroxymethyl)tetramethyldisiloxane.

The reactants, metal salt adduct (IV-A) and dihalide, are admixed in dry N,N-dimethyl formamide (approximately 2 ml. per gram of combined reactants) and are heated with stirring at 50° to 150°C for from 10 minutes to 24 hours. The resulting solution, containing suspended alkali metal halide solids, is then added in small increments with stirring to 10 volumes of water. The precipitate of bis-anthracene adduct (V) is collected by suction-filtration, washed thoroughly with water, and air-dried to constant weight. The adduct can suitably be further purified by recrystallization from an appropriate solvent and/or chromatography on alumina, activity grade I, acid or neutral. In chromatographic purification, bis-anthracene adducts are eluted rapidly from the column with the less polar solvents, e.g., benzene, benzene-hexane, or benzene-chloroform blends. Polar impurities and degradation products are usually selectively adsorbed and retained on the chromatographic column.

When the bis-anthracene adduct is obtained as a gummy or oily product on addition to water in the above procedure, it is extracted into either benzene or chloroform. The extract is backwashed thoroughly with water, dried over anhydrous magnesium sulfate, and solvent stripped. Residual adduct, generally a low melting solid or gum, is best purified further by column chromatography as described. Purification of bis-anthracene adducts is much preferred in order to obtain good yields of high purity bis (2-cyanoacrylate) monomers in the next and last step in the synthetic sequence.

In the alternate method for bis-anthracene adduct (V) formation from the 2-cyanoacryloyl halide adduct (IV-B), the latter can be prepared in situ and then reacted with the diol or it can be isolated as a pure intermediate and used as such.

For example, a reaction mixture consisting of equimolar quantities of the anthracene/2-cyanoacrylic acid adduct (III) and thionyl chloride in benzene (about 3 ml. per gram of total reactants) containing a small amount of pyridine or DMF as accelerator is stirred at from 5°C to 80°C at from one to four hours or until reaction is completed (cessation of evolution of hydrogen chloride and sulfur dioxide). To the solution of in situ produced acid chloride adduct is added dropwise, with stirring, a solution of the stoichiometric quantity of the diol and excess triethylamine dissolved in approximately an equal volume of DMF. The reaction is exothermic and can be effected at the ambient temperature or preferably, at reduced temperatures such as 5°C to 25°C. Reaction is essentially instantaneous and can be effected, depending on rate of addition and temperature control, within 15 minutes to three hours.

The reaction mixture is then diluted with additional benzene and extracted repeatedly with water. After drying the benzene extract and solvent stripping, the crude bis-anthracene adduct (V) is purified by either recrystallization from a suitable solvent or chromatography on alumina, activity grade I, acid or neutral, as hereinbefore described.

The pure anthracene/2-cyanoacryloyl chloride adduct, for example, can be prepared by reaction of the 2-cyanoacrylic acid adduct (III) with stoichiometric quantities or a 25–200% excess of thionyl chloride in refluxing benzene (about 2 to 10 ml. per gram total reactants) or other inert solvent until reaction is completed, as indicated by complete solution of the adduct (III) and cessation of evolution of hydrogen chloride and sulfur dioxide. The solvent and excess thionyl chloride are removed by distillation in vacuo and the crude acid chloride adduct purified by recrystallization from an inert solvent, such as benzene or benzene-hexane blends.

The anthracene/2-cyanoacryloyl chloride adduct (IV-B) thus prepared is dissolved in dry DMF (about 1–5 ml. per gram acid halide). With stirring, a solution of the stoichiometric quantity of the diol and an excess of triethylamine in one to five volumes of dry DMF is added dropwise over 15 minutes to three hours and at temperatures ranging from 5°C to the ambient temperatures generated from the exothermic reaction. Bisanthracene adduct (V) is isolated by quenching the reaction mixture in ten volumes of water. The precipitated bis-anthracene adduct (V) is filtered, washed well with water, dried, and purified by recrystallization from a suitable solvent or by chromatography on alumina. If the crude adduct obtained on quenching in water is a gum or oily product, it is isolated and purified by either of several procedures hereinbefore described.

Displacement of the Diene Protecting Group from Adduct V to Yield Difunctional Monomers The displacement of the protecting group can be performed by heating, but in many instances the temperature required to achieve displacement of the protecting group will risk polymerization, or at least degradation, of the difunctional monomer. Therefore, the preferred displacement is effected under lower temperature conditions in the presence of a more reactive dienophile exemplified by maleic anhydride. The bisanthracene adduct is reacted with at least an equivalent amount, preferably with an excess, and most preferably a 50–200% excess of maleic anhydride. The reaction mixture is dissolved in suitable inert solvent such as xylene or benzene, xylene being preferred. Where xylene is used the mixture is heated with stirring at about 140°C, the reflux temperature of the solvent. This heating is continued for 7–24 hours or until reaction is completed and the reaction mixture cooled to room temperature. The anthracene/maleic anhydride (A/MA) byproduct which crystallizes out in high yields is collected suitably by suction-filtration, for example, and washed thoroughly with dry $SO_2$-treated benzene. The filtrate is solvent stripped at about 50°C under reduced pressure to a residue, from which the xylene is removed by repeated additions of dry benzene and solvent stripping to a residue (monomer, excess maleic anhydride, and residual A/MA adduct).

The flask containing the crude monomer is connected to a receiver flask fitted with a condenser and a vacuum take-off adapter on top of the condenser. The receiver flask is cooled in a solid carbon dioxide bath, and the flask containing the monomer and excess maleic anhydride heated with stirring at 50° to 100°C, preferably 60°–80°C (oil bath temperature), and at 0.1–0.2mm pressure. Excess maleic anhydride readily sublimes off and is collected largely in the cooled receiver flask. Any residual maleic anhydride on the inside, upper walls of the flask can be driven off with gentle heating with a jet of heated air. The flask contents, after cooling to room temperature, are taken up in dry, $SO_2$-inhibited benzene and cooled to room temperature. Additional small amounts of A/MA adduct and polymeric by products are usually filtered off at this stage. Concentration of the filtrate and crystallization from either benzene or benzene-hexane in the cold affords the crystalline bis (2-cyanoacrylate) monomers. Where the monomer is a liquid, as much of the residual A/MA adduct is fractionally crystallized out as possible and the solution solvent stripped to give the liquid monomer.

The following detailed examples will serve to provide specific illustration of the methods of preparing the difunctional monomers.

EXAMPLE I

Preparation of 11-Cyano-11-carboisobutoxy-9,10-dihydro-9,10-endoethanoanthracene (II)

A solution of 178.2 g (1.00 mole) anthracene (>98% purity) and 153.2g (1.00 mole) isobutyl 2-cyanoacrylate (IBC) in 1000 ml. dry, $SO_2$-inhibited benzene is refluxed for 17 hours. The yellow solution is concentrated to a volume of about 600 ml. and cooled in a refrigerator. The crystalline adduct is then suction-filtered, washed with benzene and hexane, and air-dried. The yield is 224.5 g, mp. 77°–79°C. The filtrate is solvent stripped and the residue recrystallized from 350 ml. 95% ethanol to give two additional crops of product: 100.1 g, mp 92°–96°C, and 15.2 g, mp 94°–98°C. The three crops of crystals are combined and recrystallized from 95% ethanol to give several crops of purified product: 234.5 g, mp 99°–100°C; 29.0 g, mp 98.5°–100°C; 9.5 g, mp 100.5°–101.0°C. The total yield is 273 g or 82.5% of theory.

An analytical sample, recrystallized from 95% ethanol and dried over $P_2O_5$ at 60°C/0.4 mm, showed a mp of 100°–101°C.

Anal: Calcd. for $C_{22}H_{21}NO_2$: C, 79.73%; H, 6.39%; N, 4.23%. Found: C, 79.58%; H, 6.23%; N, 4.00%.

EXAMPLE II

Preparation of 11-Cyano-9,10-dihydro-9,10-endoethanoanthracene-11-carboxylic acid (III)

Into a 3-liter round bottom flask fitted with a mechanical stirrer, condenser, and heating mantle is charged 248 g (0.750 mole) anthracene/IBC adduct, 900 ml. 95% ethanol, and a solution of 73.3 g (1.13 moles) of potassium hydroxide (86.4%) dissolved in 375 ml. water. The deep red colored (sometimes a transient violet color) solution is stirred at reflux for 1.5 hours. The pale orange colored solution is quenched into 4000 ml. water. After standing at room temperature overnight, the suspension (free anthracene) is filtered and the filter cake washed thoroughly with water. The clear yellow filtrate is acidified to pH 2 by the dropwise addition with stirring of 6 N hydrochloric acid. The crystalline white solids are collected, washed with water, and air-dried to constant weight. The yield of anthracene/2-cyanoacrylic acid adduct, mp 201°–202° dec., is 189.0 g (91.8% theory). Neutralization Equivalent: Calcd: 275.31
Found: 277.8

An analytical sample, recrystallized from acetone/hexane, showed mp. 208°–209°C. dec.

Anal: Calcd for $C_{18}H_{13}NO_2$: C, 78.53%; H, 4.76%; N, 5.09%; Found: C, 78.46%; H, 4.69%; N, 5.35%

EXAMPLE III

Alternate Preparation of 11-Cyano-9,10-dihydro-9,10-endoethanoanthracene-11-carboxylic acid (III)

A mixture consisting of 356.6g (2.00 moles) anthracene (98+%) and 306.4g (2.00 moles) isobutyl 2-cyanoacrylate in 2000 ml. benzene is refluxed for 4.5 hours and cooled to room temperature. No unreacted anthracene crystallized from the solution. The latter is solvent stripped on a steam bath at water aspirator pressures to a heavy slurry of crystalline solids. Ethanol (500 ml) is added to the solids residue and the suspension stripped to a pasty solids residue again. This process is repeated with another 2× 500 ml. 95% ethanol in order to strip off the bulk of the residual benzene. The residue is diluted with 2000 ml. ethanol. A solution of 195 g (3.00 moles) of potassium hydroxide (86%w) in 1000 ml. water is then added. The reaction mixture is stirred at a moderate reflux for two hours, quenched in 7000 ml. water, and the precipitated anthracene (42.5g, mp 212°–216°C) filtered off after standing at room temperature overnight. The filtrate is acidified to pH 2.0 with 6N hydrochloric acid, and the precipitated adduct suction-filtered, washed thoroughly with water, and air-dried to constant weight. The yield of anthracene/2-cyanoacrylic acid adduct is 482.3g (88% theory), mp 200°–204° dec.

Adduct yields in five other runs ranged from 89 to 93%. Recovery of anthracene is about 5–12% w of that charged.

EXAMPLE IV

Preparation of Potassium 11-Cyano-9,10-dihydro-9,10-endoethanoanthracene-11-carboxylate (IV-A)

Into a 5 liter three-neck round bottom flask fitted with a mechanical stirrer, dropping funnel, and single probe pH electrode is charged a solution of 530 g (1.93 moles) of anthracene/2-cyanoacrylic acid adduct in 2000 ml. absolute methanol. With stirring and dropwise addition of a solution of 20% w/v potassium hydroxide in 95% ethanol, the solution pH is adjusted from 2.0 to the equivalence point, generally 9.0–9.1 pH. The suspension of solids is solvent stripped in vacuo to a pasty solids residue. Residual alcoholic solvent is removed by dilution with 500 ml acetone and stripping to moist solids. The solids are suspended in 2500 ml. acetone, stirred well at room temperature for one hour, suction-filtered, and the white solids washed thoroughly with acetone. The yield of adduct-potassium salt is 603 g (100% theory).

EXAMPLE V

Anthracene/2-Cyanoacrylic Acid Adduct - Sodium Salt (IV-A)

A solution of 19.1 g (0.0695 mole) anthracene/2-cyanoacrylic acid adduct in 100 ml. 95% ethanol is adjusted to the equivalence point by the dropwise addition of 50%w aqueous sodium hydroxide solution. Heavy crystallization of solids takes place on cooling to room temperature. The suspension is concentrated on a rotating evaporator to white solids which are dried in a desiccator over Drierite for two days and then in a vacuum oven at 60°C for three hours. The yield of adduct-sodium salt is 22.2g. The infrared spectrum is consistent with the proposed structure.

EXAMPLE VI

Anthracene/2-Cyanoacryloyl Chloride Adduct (IV-B)

A mixture consisting of 5.5 g (0.020 mole) anthracene/2-cyanoacrylic acid adduct, 2.9 ml. (0.040 mole) thionyl chloride, and 20 ml. dry benzene containing one drop of pyridine as accelerator is heated at reflux under nitrogen for two hours. On cooling to room temperature, heavy crystallization of the acid chloride adduct takes place. The benzene and excess thionyl chloride are removed on concentrating the suspension to dryness under reduced pressure with a rotating evaporator. The crude residual product is recrystallized from 1:1 dry benzene-hexane to give 4.7g of adduct, mp 77°–86°C, faint yellow needles. Concentration of the mother liquors gives another 0.7g adduct, mp. 79°–81°C. The combined yield of 5.4g is 92% of the theoretical amount.

Infrared and NMR spectral data are consistent with the structure of the adduct. Further proof of structure is obtained on conversion of the acid chloride adduct with ethanol and ethylene glycol, respectively, to the anthracene/ethyl 2-cyanoacrylate (mp 123°–125°C) and bis-anthracene/ethylene glycol bis (2-cyanoacrylate) (mp 206°–210°C) adducts.

EXAMPLE VII

Bis-Anthracene Adduct of Ethylene Glycol Bis (2-Cyanoacrylate) (V) - via Potassium Salt Adduct (IVA)

A suspension of 62.7 g (0.200 mole) anthracene/2-cyanoacrylic acid adduct-potassium salt and 18.8 g (0.100 mole) 1,2-dibromoethane in 150 ml. of dry DMF is heated with stirring to 100°C. The adduct-potassium salt is solubilized within about 10 minutes followed by the deposition of finely divided potassium bromide. After one hour at 100°C, the reaction mixture is added dropwise with stirring to 1500 ml. of water. The suspended product is stirred for one hour, collected via suction-filtration, washed thoroughly with water and lastly with a large volume of 95% ethanol (to remove entrained water and ethanol soluble impurities). The yield of bis-anthracene adduct is 48.7 g, mp 203°–206°C. A second crop of 4.4 g, mp 203.0°–206.5°C, deposited slowly from the ethanolic filtrate. The total yield is 53.1 g (92% theory).

In five runs on a 0.1 to 0.8 molar scale, the yields of adduct ranged 75–94% of theory.

EXAMPLE VIII

Bis-Anthracene Adduct of Ethylene Glycol Bis (2-Cyanoacrylate) (V) via the Sodium Carboxylate Salt Adduct (IVA)

To a stirred solution of 13.8g (0.05 mole) anthracene/2-cyanoacrylic acid adduct in 50 ml. dry DMF is added, in portions, 2.40g (0.05 mole) sodium hydride (50% in oil). Effervescence (hydrogen evolution) and a mild exotherm takes place during the in situ formation of the sodium salt. The suspension of solids is cooled to room temperature and 4.7g (0.05 mole) 1,2-dibromoethane added. The reaction mixture is stirred at room temperature for 17 hours with no apparent reaction (an aliquot deposited heavy white precipitate of acid adduct on acidification). The suspension, on heating to 100°C, becomes homogeneous. After three hours reaction at 100°C, the mixture is quenched in 400 ml. water to give 13.3 g of crude bis-adduct, mp 93°–143°C. Chromatography on 136g alumina, acid, activity grade I, and elution with benzene and benzene-chloroform gives several fractions of purified adduct. Recrystallization from either benzene or acetone/hexane gives several crops (4.0g total, 28% theory) of the bis-anthracene adduct of ethylene glycol bis (2-cyanoacrylate) showing mp. 204°–209°, 202°–205°, 205.5°–209.0°, 209°–211.5°, and 202°–205°C.

EXAMPLE IX

Bis-Anthracene Adduct of Ethylene Glycol Bis (2-Cyanoacrylate) (V) via Anthracene/2-Cyanoacryloyl Chloride Adduct Formed In Situ (IVB)

Into a 250 ml. round bottom flask fitted with a stirrer, thermometer, and nitrogen inlet adapter is charged, under nitrogen, 10.0g (0.0364 mole) anthracene/2-cynoacrylic acid adduct, 50 ml. dry benzene, 1.0 ml. DMF (as accelerator), and 4.4 ml (0.037 mole) thionyl chloride. The suspension is stirred at room temperature for 15 minutes and heated to 50°C (complete solution took place). After three hours at 60°C, the orange solution is cooled to room temperature. With stirring, a solution of 1.13 g (0.0182 mole) ethylene glycol and 3.68 g (0.0364 mole) triethylamine in 5 ml. DMF is added dropwise over 15 minutes. A moderate exotherm ensues, depositing fine solids (Et$_3$N.HCl). Since the resultant suspension is still acidic, another 1.0 ml. of triethylamine was added and the mixture stirred at room temperature for 1.25 hours. The reaction mixture is diluted with 50 ml. benzene and the solution washed four times with water. The benzene extract is dried over anhydrous magnesium sulfate, filtered, and solvent stripped to gummy yellow-orange solids (10.0g). Crystallization from acetone gives 0.7g of crude product, mp 188°–210°C. Solvent stripping of the filtrate and slurrying of the gummy residue in 100 ml. of hot ethanol gives another 5.8g, mp. 188°–197°C, of yellow solids. The two crops are combined (6.5g, 62% yield) and slurried in hot ethanol (300 ml) to give 4.1 g (39% theory) or purified product, mp 192°–201°C. Recrystallization from chloroform/ethanol gives 2.9g showing mp 201°–203°C. Further purification via chromatography on 25g alumina, acid, activity grade I, and elution with chloroform gives 1.3g of pure bis-anthracene adduct, white crystals, mp 208.5°–209.5°C.

EXAMPLE X

Bis-Anthracene Adduct of Ethylene Glycol Bis (2-Cyanoacrylate) (V) via Pure Anthracene/2-Cyanoacryloyl Chloride Adduct (IVB)

Into a reaction flask fitted with an addition funnel, thermometer, drying tube, and magnetic bar stirrer is charged 5.9g (0.020 mole) anthracene/2-cyanoacryloyl chloride adduct and 5.0 ml. dry DMF. With stirring, a solution consisting of 0.62g (0.010 mole) ethylene glycol and 3.0 g (0.030 mole) triethylamine in 5 ml. dry DMF is added dropwise over about 30 minutes. The reaction is exothermic, and the temperature is maintained at about 23°C with external cooling during the addition step. The flask contents are poured into 150 ml. water, and the gummy product is extracted into 2×50 ml. benzene. After backwashing the combined extracts with water, the extract is solvent stripped to give 4.9g of a gum. On stirring in 100 ml. boiling 95% ethanol, the gum is converted to white solids of the bis-anthracene adduct, 3.1g. mp 206°–210°C. A mixed mp with adduct prepared via the potassium carboxylate adduct and 1,2-dibromoethane showed mp 205°–210°C, or no depression.

EXAMPLE XI

Ethylene Glycol Bis (2-Cyanoacrylate); (EGBCA)

A suspension of 62.7 g (0.200 mole) anthracene/2-cyanoacrylic acid adduct-potassium salt and 18.8 g (0.100 mole) 1,2-dibromoethane in 150 ml. of dry DMF is heated with stirring to 100°C. The adduct-potassium salt is solubilized within about 10 minutes followed by the deposition of finely divided potassium bromide. After one hour at 100°C, the reaction mixture is added dropwise with stirring to 1500 ml. of water. The suspended product is stirred for one hour, collected vis suction-filtration, washed throughly with water and lastly with a large volume of 95% ethanol (to remove entrained water and ethanol soluble impurities). The yield of bis-anthracene adduct is 48.7 g, mp 203°–206°C. A second crop of 4.4 g, mp 203.0–206.5°C, deposited slowly from the ethanolic filtrate. The total yield is 53.1 g (92% theory).

In five runs on a 0.1 to 0.8 molar scale, the yields of adduct ranged 75–95% of theory.

A mixture of 57.5g (0.100 mole) bis-anthracene/EGBCA adduct, 58.8 g (0.600 mole) maleic anhydride, 200 ml. dry xylene (SO$_2$-inhibited), 0.2 g hydroquinone, and 1.0 g phosphorous pendoxide is heated at 140°–145°C for 7 hours. The resultant suspension is cooled to room temperature and the anthracene/maleic anhydride adduct (A/MA) is collected, washed well with dry benzene, and oven-dried, yield=50.7 g (92% theory), mp 260–265°C. The filtrate is solvent stripped to a liquid residue and diluted with 3 × 100 ml. dry benzene and solvent stripped each time to a residue. The semicrystalline residue is taken-up in 100 ml benzene, let stand at room temperature one hour, and filtered to give an additional 6.6 g, mp 248°–256°C, of A/MA adduct. The filtrate is solvent stripped, and the excess maleic anhydride is sublimed off at 70°C (0.2mm). Dilution of the crystalline residue with 75 ml. dry benzene gave another 1.7 g, mp 246°–258°C, of A/MA. The total recovery of A/MA adduct is 59.0 g (107% theory).

The filtrate is solvent stripped and the residue slurried in 50 ml benzene, cooled in an ice bath one hour, suction-filtered, and the white crystals washed with benzene to give 8.7 g, mp 103°–105°C, of ethylene glycol bis (2-cyanoacrylate) monomer (EGBCA).

The following additional crops of EGBCA were isolated after solvent stripping of the mother liquors, sublimation of small additional amounts of maleic anhydride, and crystallization from benzene: 3.1 g, mp 99°–103°C; 3.0 g, mp 100°–104°C; 0.3 g, mp 98°–103°C. The total yield of EGBCA is 15.1g (69% theory).

An analytical sample, recrystallized twice from benzene, showed mp 104°–105°C.

Anal: Calcd for $C_{10}H_8N_2O_4$ : C, 54.55%; H, 3.66%; N, 12.72%. Found: C, 54.75%; H, 3.69%; N, 12.61%.

The IR and NMR spectra were consistent with the proposed structure. The monomer was soluble in practically all common organic solvents, e.g., acetone, chloroform, dioxane, ethyl acetate and aromatic hydrocarbons (warm), but not in the aliphatic hydrocarbons.

EXAMPLE XII

1,3-Propanediol Bis (2-Cyanoacrylate)

In a manner analogous to Example I, a mixture consisting of 62.7g (0.200 mole) anthracene/2-cyanoacrylic acid adduct-potassium salt, 20.2 g (0.100 mole) 1,3-dibromopropane, and 165 ml dry dimethylformamide (DMF), is heated at 100°C for one hour and added dropwise with stirring to 1800 ml. water. The white solids are collected, washed with water, and air-dried to give 51.2 g, mp 95°–106°C. of adduct. A second crop, 2.9 g, mp. 91°–101°C, can be recovered from the filtrate. The total yield is 54.1g (91.5% theory). The NMR and IR spectra are consistent with the bis-adduct structure.

Reaction of 47.2 g (0.080 mole) bis-anthracene/1,3 propanediol bis (2-cyanoacrylate) adduct, 47.2 g (0.480 mole) maleic anhydride, 190 ml. dry xylene ($SO_2$), 0.1 g hydroquinone, and 0.5 g phosphorous pentoxide at 140°–145°C for four hours gives 42.9 g (97% theory) of A/MA adduct, some polymeric gel, and three crops (7.1 g, 38% theory) of product monomer showing mp 74°–78°, 75°–77° and 64°–77°C. Recrystallization from dry benzene gave additional polymer (orange gum) and 6.1 g (33% theory) of pure product monomer, mp 79°–81°C.

EXAMPLE XIII

1,4-Butanediol Bis (2-Cyanoacrylate); (1,4-BDBCA)

Similarly, 15.7 g (0.05 mole) anthracene/2-cyanoacrylic acid adduct-potassium salt and 5.4g (0.025 mole) 1,4-dibromobutane in 40 ml. dry DMF are heated one hour at 100°–105°C and quenched in 400 ml. water to yield 13.1 g, mp. 162°–172°, and 1.2 g, mp. 166°–169°C, of crude adduct. Recrystallization from chloroform/ethanol gives 12.7 g (84% theory) of purified bis-adduct, mp 168°–175°C.

TLC (1:1 $CHCl_3$ /$C_6H_6$): Rf 0.34 + trace amounts of impurities. All TLC procedures described herein were conducted on Eastman 6060 Silica Gel chromatogram sheet.

Recrystallization of the 12.7 g adduct from 150 ml. benzene gives 10.9 g white crystals, mp. 198°–203°C, the higher melting polymorphic form. Concentration of the mother liquors gives two of the polymorphic forms showing mp 175°–176°C and mp 198°–206°C.

It should be noted that mixtures of two or more polymorphic forms of bis-adduct are generally isolated. This gives rise to a number product-crops showing wide melting point ranges (e.g. 164°–201°C). Heating in various solvents can often suffice to convert one form into another.

A mixture of 30.2 g (0.05 mole) bis-anthracene/1,4-butanediol bis (2-cyanoacrylate) adduct, 29.4 g (0.300 mole) maleic anhydride, 100 ml. dry xylene ($SO_2$), 0.1 g hydroquinone, and 0.5 g of phosphorous pentoxide is heated at 137°–143°C for 7 hours. Work-up according to the general scheme gives 27.2 g (99% theory) of A/MA adduct and a total of five crops (7.4 g, 60% theory) of monomer, mp. 76–79, 76–78, 75–82, 77–79. Recrystallization from toluene and toluene-hexane gives 4.5 g, mp 77.5–79.0 °C, and 0.7 g, mp 78.5°–80.0°C, of pure 1,4-BDBCA monomer (42% theory).

EXAMPLE XIV trans-2-Butene-1,4-Diol Bis (2-Cyanoacrylate); (t-1,4-BDBCA)

Reaction as above of 62.7 g (0.200 mole) anthracene/2-cyanoacrylic acid adduct-potassium salt and 21.4 g (0.100 mole) trans-1,4-dibromo-2-butene in 160 ml. dry DMF at 100°C for one hour followed by addition to 1600 ml. water gives 60.1 g, mp. 93°–100°C. and 1.9 g, mp 93°–95°C, of methanol-washed adduct. Recrystallization of the combined solids from benzene give two crops of adduct: 25.3 g, mp 104°–107°C, and 11.7g, mp 145°–148°C. A third crop, 11.4 g, mp 148°–150°C, is obtained on addition of hexane to the mother liquors. Total yield, 48.4 g (80% theory).

The first crop (25.3 g), on suspension in 250 ml boiling ethanol and filtration, yields 19.4 g, mp. 178°–179°C., of the higher melting polymorphic form. Combination of the second and third crops (23.1g) and slurrying in hot ethanol gives another 20.8 g, mp. 149°–152°C, of the lower melting polymorph. Further work-up of various mother liquors gives 2.3 g white crystals (from benzene) showing mp 101.5°–108°C. All three polymorphic forms of the bis-adduct showed Rf 0.5 on TLC in 1:1 $CHCl_3/C_6H_6$.

A mixture consisting of 36.2 g (0.06 mole) bis-anthracene/trans-2-butene-1,4-diol bis (2-cyanoacrylate) adduct, 35.3 g (0.36 mole) maleic anhydride, 120 ml. dry xylene ($SO_2$), 0.12 g hydroquinone, and 0.6 phosphorous pentoxide is stirred at gentle reflux for 7 hours and cooled to room temperature. The crystalline A/MA adduct is collected, washed with dry benzene, and dried in vacuo; yield = 30.3 g (92% theory), mp 256°–257°C. The filtrate is solvent stripped to a liquid residue which is redissolved in several portions of dry benzene and solvent stripped to a residue each time. The residue, on crystallization from 50 ml. benzene in an ice bath, gives 6.4 g of crude monomer, mp 108°–120°C. The crude monomer is slurried in 50 ml. boiling benzene and filtered hot from the two crops of insoluble A/MA adduct (2.6 g, mp 257°–260°C and 0.4g, mp. 255°–260°C). The benzene solubles, on concentration and crystallization from benzene/hexane, afford 2.0 g, mp 106°–108°, and 0.6 g, mp 105°–108°C of additional monomer.

The mother liquor from the 6.4 g monomer fraction is solvent stripped and additional maleic anhydride sublimed off at 80°C (0.1 mm). Crystallization of the residue from 25 ml. benzene gives 6.3 g, mp. 104-105°C (162° clear melt), and 2.9 g, mp. 103°–104°C, of monomer. The total yield of t-1,4-BDBCA monomer is 11.8 g (80% theory).

Recrystallization from benzene of combined monomer (19.1g) from two runs gives some polymeric solids and 12.8 g of pure t-1,4-BDBCA, mp 105°–107°C, white needles. Concentration of the mother liquors gives two additional crops; 0.9 g, mp 100°–105°C, and 1.3 g, mp 93°–105°C.

The total yield of A/MA adduct recovered is 33.3g (100% theory).

EXAMPLE XV 2,5-Hexanediol Bis (2-Cyanoacrylate); (2,5-HDBCA)

A mixture of 62.7g (0.200 mole) of anthracene/2-cyanoacrylic acid adduct-K salt, 24.4 g (0.100 mole) 2,5-dibromohexane, and 150 ml of dry DMF are heated at 100°C for one hour and added dropwise to 1500 ml water. The white solids are collected, washed with water, and air-dried. The yield of bis-adduct, mp 84°–86°C, is 60.0 g (94.8% theory).

Bis-adduct from another run showed mp. 87°–92°C; TLC (1:1 $CHCl_3/C_6H_6$): Rf 0.6.

A mixture consisting of 56.0 g (0.0885 mole) bisanthracene/2,5-HDBCA adduct, 52.0g (0.531 mole) maleic anhydride, 0.1 g hydroquinone, and 1.0 g phosphorous pentoxide in 220 ml. dry, $SO_2$ inhibited xylene is heated at 138°–142°C for 8 hours, cooled to room temperature, and filtered to give 31.7 g, mp 264°–268°C, of the A/MA adduct. After solvent stripping to remove residual xylene, the excess maleic anhydride is sublimed off at 65°–80°C/0.2 min. The orange gummy residue is recrystallized from benzene in the cold to give another 5.5 g, mp 261°–267°C, of A/MA adduct. Concentraton of the filtrate and crystallization from benzene/hexane gives 0.8 g of white solids showing mp 73°–190°C. Further concentration and cooling give additional white solids. The latter are collected, washed successively with benzene, 1:1 benzene/hexane, and hexane to give 1.6 g of product monomer, mp 80.0° – 80.5°C.

EXAMPLE XVI 1,3-Bis(Hydroxymethyl) Benzene Bis (2-Cyanoacrylate)

A mixture consisting of 15.6 g (0.050 mole) anthracene 2-cyanoacrylic acid adduct-K salt and 4.3 g (0.025 mole) 1,3-bis (chloromethyl) benzene in 40 ml. dry DMF is heated at 100°C for one hour and added dropwise, with stirring, to 500 ml. water. The fine solids are collected by gravity filtration, washed with water and methanol, and air-dried to give 10.5 g pale yellow solids, mp 105°–110°C. Two additional crops, 0.2 g, mp 113°–118°C, and 2.3 g, mp 98°–104°C, are obtained by concentration of the methanolic washes. The total yield is 13.0 g (82% theory). TLC (1:1 $CHCl_3/C_6H_6$): Rf 0.6 (bis-adduct) + Rf 0.9 (anthracene) + traces of polar impurities (for all three crops).

In another run on a 0.05 mole scale, the yield of crude bis-adduct, mp. 86°–88°C, was 30.9 g (98% theory), white solids.

A mixture consisting of 30.0 g (0.0474 mole) bisanthracene adduct/ 1,3-bis (hydroxymethyl) benzene bis (2-cyanoacrylate), 27.8 g (0.284 mole) maleic anhydride, 0.1 g hydroquinone, and 0.5 g phosphorous pentoxide in 125 ml. dry xylene is heated at 139°–141°C for 5 hours, cooled to room temperature, and suction-filtered to give 26.1 g, mp 257°–259°C, of A/MA adduct. Solvent stripping of the filtrate and crystallization of the residue from benzene gives another 3.5 g, mp 258°–260°C, of A/MA adduct. The mother liquor is solvent stripped and the excess maleic anhydride sublimed off at 60°–65°C/0.1-0.2mm. The semi-crystalline residue (11.4g) is taken-up in 50 ml. hot benzene, the solution decanted from some insolubles (3.5 g, mp>300°C) and cooled to give another 1.3 g, mp 260°–262°C, of A/MA adduct. The filtrate is concentrated in vacuo to give 6.2 g (44% theory) of crude monomer as a pale orange liquid. IR and NMR analysis indicated the presence of considerable anhydride-containing and other unknown impurities.

EXAMPLE XVII 1,3-Bis(hydroxymethyl)tetramethyldisiloxane Bis (2-Cyanoacrylate)

A mixture consisting of 125.4 g (0.400 mole) anthracene/2-cyanoacrylic acid adduct-K salt and 46.2 g (0.200 mole) 1,3-bis (chloromethyl) tetramethyldisiloxane in 340 ml. dry DMF is heated at 100°C for one hour and quenched in 3400 ml water. The gummy product is twice extracted into 500 ml portions of benzene, and the combined extracts are washed with 4×250 ml water, 1×250 ml saturated sodium chloride solution, and then dried over magnesium sulfate. The dried solution is concentrated to about 400 ml and filtered slowly through a column of 500 g. alumina, neutral, activity I, at a fast dropwise rate and eluted further with an additional 1000 ml benzene. Solvent stripping gives 98.9g (70% theory) of the bis-adduct as a colorless gum.

The NMR and IR spectra are consistent with the proposed structure. Some extraneous peaks due to impurities are seen in the NMR scan but not in the IR spectrum.

In another rum using 1,3-bis (bromoethyl) tetramethyldisiloxane as reactant, the purity of the crude bis-adduct isolated via benzene extraction is very similar to that obtained from the dichloro reactant. Chromatography on alumina, acid, activity I, affords a 64% recovery of bis-adduct on elution with 1:1 benzene-hexane, benzene, 1:1 benzene-chloroform and chloroform. Only a marginal improvement in purity is obtained for some fractions, and there is strong indication of product degradation on the column.

A mixture consisting of 52.7 g (0.0743 mole) bisanthracene adduct/1,3-bis (hydroxymethyl) tetramethyldisiloxane bis (2-cyanoacrylate), 43.8 g (0.446 mole) maleic anhydride, 0.1 g hydroquinone, and 1.0 g phosphorus pentoxide in 190 ml. dry, $SO_2$-inhibited xylene is heated at a gentle reflux (140 °C) for 8 hours, cooled to room temperature, and filtered to give 30.6 g, mp 258°–262°C, of A/MA adduct. The filtrate is solvent stripped to a dark orange syrup which is taken-up in 50 ml. benzene and filtered to give an additional 4.2 g, mp. 258°–261°C, of A/MA adduct. The resultant filtrate is concentrated to a syrupy residue again and the excess maleic anhydride is sublimed off at 65°–75°C/0.2mm. The pot contents are slurried in 25 ml. benzene and filtered to afford 1.0 g, mp 235°–258° C. of A/MA adduct. The mother liquors are concentrated to about 50 ml. and diluted with about 25 ml. hexane to give, in two stages, an additional 0.3 g. and 0.2 g. of A/MA adduct. A final solvent stripping of the filtrate gives 22.3 g (85% theory) of the bis (2-cyanoacrylate) monomer, a brown-orange syrupy liquid. The total A/MA adduct yield is 36.3 g (89theory).

IR and NMR assay confirmed the identity of the monomer but indicated contamination by some residual A/MA adduct and other unknown silicone-containing impurities.

EXAMPLE XVII

In a manner analogous to the above examples, the following difunctional monomers are also prepared:

methylene glycol bis (2-cyanoacrylate) from methylene iodide;

1,3-butanediol bis (2-cyanoacrylate) from 1,3-dichlorobutane;

1,5-pentanediol bis (2-cyanoacrylate) from 1,5-dichloropentane;

1,6-hexanediol bis (2-cyanoacrylate) from 1,6-dichlorohexane;

1,6-hexanediol bis (2-cyanoacrylate) from 1,6-dibromohexane;

1,7-heptanediol bis (2-cyanoacrylate) from 1,7-dibromoheptane;

1,8-octanediol bis (2-cyanoacrylate) from 1,8-dibromooctane;

1,9-nonanediol bis (2-cyanoacrylate) from 1,9-dichlorononane;

1,10-decanediol bis (2-cyanoacrylate) from 1,10-dibromodecane;

1,12-dodecanediol bis (2-cyanoacrylate) from 1,12-diclorododecane;

1,12-dodecanediol bis (2-cyanoacrylate) from 1,12-dibromododecane, 2-butyne-1,4-diol bis (2-cyanoacrylate) from 2-butyne-1,4-diol;

neopentyl glycol bis (2-cyanoacrylate) from neopentyl glycol;

1,4-bis (hydroxymethyl) benzene bis (2-cyanoacrylate) from 1,4-bis(chloromethyl) benzene; and Bis(4-hydroxybutyl) ether bis (2-cyanoacrylate) from bis (4-hydroxybutyl) ether.

EXAMPLE XVIII

Cyclopentadiene/IBC Adduct (Isobutyl 2-Cyano-5-Norbornene-2-Carboxylate) (II)

To first prepare the cyclopentadiene monomer, dicyclopentadiene (95%, Enjay Chemical) is charged into a round bottom flask fitted with a magnetic bar stirrer, 30 cm. Vigreux column packed with Berl saddles, and a distillation head/receiver. The dimer is heated with stirring, under nitrogen and at atmospheric pressure, to reflux. After collecting a small forerun cut at bp 28°–36°C, the cyclopentadiene monomer is collected at bp 36°–40°C in a Dry Ice cooled receiver. The monomer is used immediately in the following step.

Into a one-liter round bottom flask fitted with a thermometer, condenser, Drierite drying tube, dropping funnel, nitrogen inlet adapter, and a magnetic bar stirrer is charged 92.2g (1.40 moles) cyclopentadiene monomer (freshly distilled), 500 ml dry benzene, and 0.1g p-methoxyphenol. The solution is cooled with stirring to 5°C and to this is added, over one hour and at 5°–15°C, 214g (1.40 moles) isobutyl 2-cyanoacrylate (inhibited with excess $SO_2$). The exotherm subsides quickly after the addition of isobutyl 2 -cyanoacrylate The ice bath is removed and the solution stirred at room temperature overnight. The solution is solvent stripped to give 312.6g (102% theory) of crude adduct, a colorless liquid. The latter is inhibited with 0.1g p-methoxyphenol and distilled in vacuo through a 6 inch Vigreux column. Pure isobutyl 2-cyano- 5-norbornene-2-carboxylate is collected at bp 91°C (0.4mm) – 96°C (0.6mm). The yield of colorless distillate is 287.0g (94% theory).

TLC: 1:1 $C_6H_6/CHCl_3$, Rf 0.7; $C_6H_6$, Rf 0.84 (all TLC procedures were conducted on Eastman 6060 Silica Gel chromatogram sheets). On the basis of NMR, there is approximately a 60/40 ratio of the two expected stereoisomers.

EXAMPLE XIX

Cyclopentadiene/2-Cyanoacrylic Acid Adduct (2-Cyano-5-Norbornene-2-Carboxylic Acid) (III)

To a solution of 250 g (1.14 moles) isobutyl 2-cyano-5-norbornene-2-carboxylate (IBC/CPD adduct) in 1000 ml. 95% ethanol is added a solution of 112 g (1.71 moles) of potassium hydroxide (86%w) in 1000 ml. water. The solution is refluxed on a steam bath for one hour, diluted with 3500 ml. water, and extracted with 2 × 400 ml. benzene to remove any unreacted ester. The aqueous phase is acidified to pH 1 with 6 N HCl and the oily product extracted into 4 × 200 ml. chloroform. The combined extracts are backwashed with 3 × 200 ml. water (which removed the orange color), dried over anhydrous sodium sulfate, and solvent stripped to give 182.3g (98% theory) of the crude adduct, a pale orange syrupy liquid. Crystallization from benzene/hexane gives three crops of purified 2-cyano-5-norbornene-2-carboxylic acid: (1) 89.7 g, mp 87.5°–92°C, (2) 34.2 g, mp 87.5°–96.5°C, and (3) 15.9 g, mp. 85°–90°C.

A sample, mp 88°–96°C, from an earlier run showed spectral characteristics consistent with the proposed structure. The NMR spectrum shows that the ratio of stereoisomers is now 80/20 (vs 60/40 in the ester precursor).

Neutralization Equiv. (mp 88°–96°C): Found, 163.9; Calcd, 163.2

EXAMPLE XX

Cyclopentadiene/2-Cyanoacrylic Acid Adduct - Potassium Salt (Potassium 2-Cyano-5-Norbornene-2-Caroxylate) (Iv-A)

A stirred solution of 134.0 g (0.822 mole) 2-cyano-5-norbornene-2-carboxylic acid in 400 ml. anhydrous methanol is adjusted from pH 1.5 to pH 9.0 (equivalence point) by the dropwise addition of a solution of 20% w/v potassium hydroxie in 95% ethanol. The solution is solvent stripped to a gum which is taken up several times in acetone and concentrated to a gummy residue each time. The gum, on trituration with 1:1 acetone - benzene (900 ml), gives white solids. Filtration, washing with acetone, and air-drying gives 92.5 g of product, mp 188°–189°C dec. Concentration of the filtrate to 400 ml gives another 19.9 g, mp. 188°C dec. Solvent stripping to a syrupy residue and crystallization from acetone/hexane and acetone gives two more crops of product; mp 22.6 g. mp. 188.0°–188.5°C dec. and 21.2 g, mp. 190°–191°C dec. The total yield of potassium 2-cyano-5-norbornene-2-carboxylate is 156.2 g (94% theory).

EXAMPLE XXI

Bis-Cyclopentadiene Adduct/Ethylene Glycol Bis(2-Cyanoacrylate); [Ethylene Glycol Bis(2-Cyano-5-Norbornene-2-Carboxylate)]

A mixture of 40.3g (0.200 mole) potassium 2-cyano-5-norbornene-2-carboxylate, 18.8g (0.100 mole) 1,2-dibromoethane, and 118 ml. dry DMF is heated at 100°C for one hour and quenched in 1200 ml. water. The orange gum is extracted into 1 × 200 ml. and 2 × 100 ml. chloroform, and the combined extracts are washed with 4 × 100 ml. water, dried over a mixture of magnesium sulfate and decolorizing carbon, filtered, and solvent stripped to an orange syrupy liquid (34.0g, 96%). The crude product is chromatographed on 200 g alumina, neutral, activity I, and eluted with benzene (600 ml) to give 23.9g (68% theory) of bis-adduct, a colorless syrupy liquid. The NMR spectra of the 34.0g and 23.9g fractions were essentially identical and consistent with the proposed structure. The yield reduction is due to product degradation on the column.

EXAMPLE XXII

Ethylene Glycol Bis (2-Cyanoacrylate) (EGBCA) via Bis-Cyclopentadiene Adduct/EGBCA (V)

A mixture consisting of 10.0g (0.0284 mole) bis-cyclopentadiene/ethylene glycol bis (2-cyanoacrylate) adduct, 16.7g (0.170 mole) maleic anhydride, 0.1g hydroquinone, and 0.5g phosphorus pentoxide in 53 ml. dry xylene ($SO_2$ inhibited) is refluxed at 138°–142°C for seven hours and cooled to room temperature. A small amount of white solids (0.8g, mp 243°–245°C), probably homopolymer, is collected via suction-filtration. The filtrate is solvent stripped to a yellow syrup from which the residual xylene is removed by periodic additions of benzene and solvent stripping. The excess maleic anhydride is sublimed off at 70°–75°C/0.1mm. The residual syrup, which crystallized on cooling, was taken-up in 75 ml. hot benzene, filtered from the insoluble gelatinous polymer (0.8g), and concentrated to a yellow syrup (14.1g). The latter is triturated several times with hot hexane and benzne/hexane mixtures. The extracts give several crops of white needles on cooling to room temperature or below: 1.6 g. mp. 105°–122°C; 3.8g, mp. 74°–122°C; 0.5g, mp 86°–136°C; 0.2g, mp. 87°–136°C, 0.2g, mp. 119°–136°C. The residual nonextractable yellow syrup afforded 2.0g (32% theory) of EGBCA monomer, mp 96°–103°C (mixed up 100°–104°C), on crystallization from benzene in the cold.

EXAMPLE XXIII

Norbornadiene/Isobutyl 2-Cyanoacrylate Adduct (II); 4-Carboisobutoxy-4-cyanotetracyclo[$4.2.1.0^{2,9}.0^{3,7}$] nonane.

Into a 100 ml. round bottom flask fitted with a condenser, thermometer, magnetic stirring bar, and a Drierite filled drying tube is charged 18.4 g (0.200 mole) norbornadiene, 30.6 g (0.200 mole) isobutyl 2-cyanoacrylate (inhibited with excess sulfur dioxide), and 0.1 g hydroquinone monomethyl ether (MEHQ). The solution is stirred and heated under a nitrogen atmosphere to 110°C. After 15 minutes at 100°C., the solution became cloudy, more viscous, and the reflux rate diminished. The mixture is then heated to 150°C. and maintained at this temperature for 24 hours. The solution is cooled to room temperature, diluted with 200 ml. hexane, filtered to remove polymeric solids, and the filtrate solvent stripped to a dark orange syrupy residue. The lattter is dissolved in 200 ml. acetone and to the resultant solution is added 800 ml. of an aqueous solution containing 96 g. of potassium permanganate and 96 g. magnesium sulfate. After several minutes, the excess potassium permanganate is destroyed by bubbling sulfur dioxide gas into the solution. The manganese dioxide precipitate is filtered and the solids washed thoroughly with acetone. After dilution of the filtrate with one-half of its volume with water, the product is extracted into chloroform. The extract is back-washed with 3 × 500 ml. water, dried over anhydrous magnesium sulfate, filtered, and solvent stripped under reduced pressure to give 27.2 g (56% theory) of crude adduct. Distillation affords 24.0 g (49% theory) of the pure norbornadiene/isobutyl 2-cyanoacrylate adduct, b.p. 110°–112°C. (0.4 mm), a colorless liquid.

EXAMPLE XXIV

Norbornadiene/2-Cyanoacrylic Acid Adduct (III); 4-Cyanotetracyclo [$4.2.1.0^{2,9}.0^{3,7}$]nonane-4-carboxylic acid.

Into a flask fitted with a condenser and magnetic stirring bar is charged 12.3 g (0.05 mole) norbornadiene/isobutyl 2-cyanoacrylic acid adduct and a solution of 4.9 g 86% potassium hydroxide (0.075 mole) in 75 ml. of water. After heating at reflux for 1.5 hours, the solution is cooled to room temperature and extracted with 2 × 25 ml. of hexane to remove any non-saponified adduct. The aqueous phase is acidified to pH 2 with 6 N hydrochloric acid and the liberated oily product is taken up in 100 ml. ethyl acetate. The extract is filtered to remove some white insoluble solids (0.9g., m.p. 182°C.) and the filtrate washed with 3 × 25 ml. water, 1 × 25 ml. saturated sodium chloride solution, and solvent stripped in vacuo to a pale yellow, viscous oil (8.7 g.). Crystallization of the oily product from benzene/hexane in the cold affords 4.2 g of the norbornadiene/2-cyanoacrylic acid adduct, white cyrstals, m.p. 83°–86°C. Another 3.0 g. of adduct, m.p. 81°–84°C., is obtained on concentration of the mother liquors and cooling. The combined crops of adduct are recrystallized from 1:2 benzene/hexane to afford 5.9 g of pure adduct, white crystals, m.p. 81°–83°C. Anal: Neutralization Equivalent: Found, 189.06 g/equiv.; Calculated (Theory), 189.22 g/equiv.

EXAMPLE XXV

In a manner analogous to that of Example XXI, the difunctional monomers specified in Example XVII are prepared from the corresponding bis (2-cyano-5-norbornene-2-carboxylic acid) esters of the diols.

Thus, having described the preparation of the bis esters of this invention, specific embodiments which utilize these bis esters will now be described.

In the broadest aspect, the individual difunctional bis (2-cyanoacrylate) monomers can be either homopolymerized or copolymerized and employed as adhesives for joining or filling the various materials previously noted, or can be used as protective coatings on various materials, such as paper goods. Those difunctional monomers which are crystalline solids at room temperature require dissolution in some solvent before they can advantageously be employed as an adhesive or coating material. Such a solvent may include a comonomer of this invention which is liquid at room temperature, such as 1,3-bis (hydroxymethyl) tetramethyldisiloxane bis (2-cyanoacrylate); other monomers which act as a solvent for the bis (2-cyanoacrylate) and can be copolymerized therewith; or if one or more of only the solid bis (2-cyanoacrylate) monomers are employed, a solvent such as the aromatic hydrocarbons or other mutually miscible aprotic solvents. The use of these latter solvents is not an entirely desirable alternative, however, since such solvents do not polymerize or copolymerize but merely are entrapped in the polymerized material, thus not contributing to is desirable properties.

In preferred embodiments the monomers of this invention are employed in comonomer compositions which comprise admixtures of the bis (2-cyanoacrylates) and at least one polymerizable monofunctional ester of 2-cyanoacrylic acid. Initiation and propagation of polymerization of such compositions is accomplished by means of an anionic catalyst as hereinafter described or, alternatively, by thermal or other means recognized as being suitable for initiating the polymerization of monomers having the cyanoacrylate function present in their structure.

Desirable esters of 2-cyanoacrylic acid include alkyl esters of 2-cyanoacrylic acid, wherein the alcoholic moiety of the ester is either an alkyl group of from 1–16 carbon atoms, a cyclohexyl group, or a phenyl group. The monofunctional 2-cyanoacrylate, being a liquid at room temperature, functions as a reactive comonomer and solvent for the difunctional bis (2-cyanoacrylates). The bis (2-cyanoacrylate) monomer is an effective crosslinking agent when included in amounts as small as 1% by weight based on the total weight of the monomers present. Generally, improvements in polymer properties such as breaking strength are observed when higher concentrations of crosslinking difunctional monomers are included, up to and including the maximum amount soluble in the monofunctional 2-cyanoacrylate ester.

In Table I, illustrative maximum solubilities of various difunctional monomers of this invention in isobutyl 2-cyanoacrylate are noted. Once one has determined which difunctional monomer and which monofunctional monomer he desires to include in blend of these monomers, it is a simple task to determine the maximum solubility of the difunctional monomer in that specific ester of 2-cyanoacrylic acid. Less than the maximum amount soluble can, of course, be employed, while still obtaining excellent crosslinking with the ester of 2-cyanoacrylic acid and giving a polymer having improved adhesive properties.

In order to initiate the polymerization reaction of either the monomers or the comonomer blends of this invention, it is suitable to use a basic catalyst such as a metal hydroxide, a basic salt, ammonia, or organic amines. Other weak nucleophiles such as water and alcohol also can initiate reaction. Polymerization by free radical and thermal means is also possible, but anionic initiation is preferred and favored because of the presence of strong electron withdrawing groups in the cyanoacrylate monomer structure.

In general, those catalysts or initiators that are suitable for the polymerization of esters of 2-cyanoacrylic acid, whether chemical in nature or in the form of radiant energy, are suitable for initiating and propagating polymerization of the monomers of this invention whether as homopolymers, or copolymers from monomer blends thereof, or in combination with esters of 2-cyanoacrylic acid.

Preferred catalysts are the organic amines, especially tertiary amines; specific examples of which include N,N-dimethylaniline, N,N-diethylaniline, N-methylbenzylamine, triethanolamine, triethylamine, diethanolamine, diethylamine, 2-picoline, 4-picoline, tributylamine, 4-ethylpyridine, pyridine, N,N-diethylethylenediamine, N,N-dimethyl-p-toluidine, N,N-diethyl-1-napthylamine, and hexamethylenediamine. Of these, N,N-dimethyl-p-toluidine is preferred.

Only a trace amount, e.g., 0.005% by weight of catalyst is necessary to initiate polymerization. Yet, to evenly distribute such a trace amount throughout a monomer, or comonomer blend, is rather difficult. Therefore, a convenient and preferred technique for catalysis of filled cyanoacrylate compositions is to incorporate the trace amounts of amine catalyst required on the filler particles. On stirring a monomer/filler blend, the catalyst diffuses from the filler particls into the composite mixture. The catalyzed composition proceeds through an initial induction period, during which the mixture maintains a relatively constant working viscosity. This is followed by a gellation stage which in turn is rapidly followed by an almost instantaneous transition (in 5–15 seconds) to a hard composite mass.

Unfilled bis (2-cyanoacrylate) monomers, or their comonomer blends with other cyanoacrylates, are catalyzed by contacting the neat monomer with a very small amount of alumina which has been pretreated with a high concentration of the amine catalyst, generally 4% by weight based on the alumina. The amine catalyst diffuses from the alumina particles into the monomer phase. The catalyzed monomer phase is separated from the very small amount of alumina catalyst particles by allowing them to settle out to the bottom of the mixing

TABLE I

| Maximum Solubility of Bis (2-Cyanoacrylate) Monomers in Isobutyl 2-Cyanoacrylate at Room Temperature. | |
|---|---|
| | % By Weight(approx.) |
| Ethylene glycol bis(2-cyanoacrylate) | 5 |
| 1,3-Propanediol bis (2-cyanoacrylate) | 9 |
| 1,4-Butanediol bis (2-cyanoacrylate) | 15 |
| trans-2-Butene-1,4-diol bis (2-cyanoacrylate) | 7 |
| 1,6-Hexanediol bis (2-cyanoacrylate) | 34 |
| 2,5-Hexanediol bis (2-cyanoacrylate) | 25 |
| 1,8-Octanediol bis (2-cyanoacrylate) | 17 |
| 1,9-Nonanediol bis (2-cyanoacrylate) | 32 |
| 1,10-Decanediol bis (2-cyanoacrylate) | 7 |
| 1,12-Dodecanediol bis (2-cyanoacrylate) | 6 |
| 1,3-bis (Hydroxymethyl) tetramethyldisiloxane bis (2-cyanoacrylate) | ∞ | vessel, or even removed if desired, prior to gellation. The time required for the catalyzed monomer to reach the gellation and polymerization stage can be varied by modifying the monomer/catalyst carrier contact time, weight ratio of monomer to catalyst carrier, catalyst concentration on the alumina particles, and sulfur dioxide inhibitor level in the monomer.

In preparing compositions that are to be worked or shaped after initiating catalysts, such as those employed in dental applications, the period from the onset of mixing to the beginning of the gellation stage (gel time) is the time period during which the composition can be worked. After the gellation stage has begun, through to a period of transition to a hard set material, the polymerizing material ought not be disturbed. For pit and fissure sealant formulations gel times of 1–2 minutes and transition times of 5–15 seconds are desirable. Specific gel and transition periods can be obtained by decreasing and increasing the amounts of catalyst and the amount of monomer inhibitor, such as sulfur dioxide, or the balance between catalyst and inhibitor. The use of sulfur dioxide inhibitors in 2-cyanoacrylate systems is well known and need not be discussed here in detail.

The comonomer blends of this invention employing a monofunctional monomer consisting of an ester of 2-cyanoacrylic acid can be utilized either in filled or unfilld systems. When a filler is employed, it can be any material resistant to the abrasion, erosion, or corrosive attack by substances that are likely to contact the polymerized filled material. Such fillers can be powdered metal or metal oxides, silica or silicacious materials, carbides, and the like. For dental applications the preferred fillers are quartz and alumina. Other fillers such as glass and polyethylene may be used. For dental and other applications the particle size should substantially be in the range of from 1 to 100 microns. Larger particles are not deleterious, but do not provide a smooth textured material. Similarly, smaller particles are not desirable since they are too small to serve as a good aggregate. The filler if used should be employed in amounts sufficiently large to be of value, e.g., at least 10% by weight, and should not be used in so large a quantity, e.g., more than 85% by weight, that all the filler particles are not wetted by the monomer or monomer blend. Generally, a desirable quantity of filler will be in the range of from 50% to 80% by weight. These percentages of filler are based on the total weight of monomers and filler present in the composition.

In Table II there is summarized the lap shear adhesion and the breaking strength properties of various polymeric compositins prepared from both filler and unfilled blends compositions difunctional monomers and isobutyl 2-cyanoacrylate. Each blend was catalyzed with N,N-dimethyl-p-toluidine by the appropriate technique as heretofore discussed.

The compositions set forth in Table II can be suitably employed as pit and fissure sealants. The patient's mouth is first rinsed with an oral antiseptic and then with water. The teeth are isolated with cotton rolls, thoroughly dried with an air syringe, and etched for approximately one minute with phosphoric acid. The patient then rinses his mouth thoroughly with water to remove the acid from the tooth surfaces. The teeth are again isolated with cotton rolls and again thoroughly dried. The pit and fissure sealant prepared according to the foregoing description is then applied by conventional techniques.

Breaking strengths are measured by compression testing on an Instron tester at a strain rate of 0.02 inches per minute. Cylindrical test specimens, measuring 0.15 inch in diameter and 0.30 inch length, are prepared by pouring catalyzed monomer compositions into Teflon molds, allowing the mass to polymerize, extruding the specimens from the molds, polishing the ends flat and smooth, and conditioning the specimens in water at 100°F for 24 hours prior to compression testing. The stress/strain curve on compression consists of a brittle component and a viscoelastic type component which is evident beyond the yield point. Breaking strengths reported are calculated from the compressive force values where the specimens undergo a physical breakdown, as determined instrumentally, and are invariably of greater magnitude than the yield strengths at the proportional limit.

Shear adhesion measurements were made on carefully cleaned steel plates (0.05 inch × 2 inches × 0.1 inch) cemented together to give a 0.5 × 0.5 inch lap joint. A 37.5 gram weight was placed on top of the joined surfaces until a firm adhesive bond was established. The specimens were conditioned at room temperature for 24 hrs. and the shear adhesive force measured on an Instron tester at a strain rate of 0.5 inch per minute.

TABLE II

STRENGTH PROPERTIES OF FILLED AND UNFILLED CYANOACRYLATE POLYMER COMPOSITIONS

| Difunctional Bis (2-Cyanoacrylate) of the Diol - | % Monomer Content Based On Total Weight Monomers Present In Composition | | Filler Content Based On Weight Total Composition | | Lap Shear Adhesion PSI | Breaking Strength PSI | |
|---|---|---|---|---|---|---|---|
| | Percent Difunctional Monomer | Percent Isobutyl-2-(Cyanoacrylate) | Alumina Filler % By Weight | Quartz Filler % By Weight | | Range | Average |
| — | 0 | 100 | 72–75 | 0 | 1370 | 5470–8220 | 6850 |
| — | 0 | 100 | 0 | 80 | — | 6470–6960 | 6760 |
| — | 0 | 100 | 0 | 0 | 660 | 5220–6840 | 6130 |
| Ethylene glycol | 4 | 96 | 75 | 0 | 1410 | 6520–7460 | 6860 |
| Ethylene glycol | 20 | 80 | 72 | 0 | — | 8000–8970 | 8380 |
| Ethylene glycol | 4 | 96 | 0 | 80 | — | 6880–7860 | 7410 |
| Ethylene glycol | 4 | 96 | 0 | 0 | 1150 | 4030–22920 | 7070 |
| 1,3-Propanediol | 9 | 91 | 73.5 | 0 | — | 5540–7650 | 6560 |
| 1,3-Propanediol | 9 | 91 | 0 | 0 | 1260 | 5230–7490 | 5840 |
| 1,4-Butanediol | 15 | 85 | 72 | 0 | — | 8410–9350 | 8710 |
| 1,4-Butanediol | 15 | 85 | 0 | 0 | 1160 | 5420–10600 | 7880 |
| Trans-2-butene-1,4-diol | 7 | 93 | 72 | 0 | — | 7840–8520 | 8130 |
| Trans-2-butene-1,4-diol | 7 | 93 | 0 | 0 | 1420 | 5870–7710 | 6460 |
| 2,5-Hexanediol | 25.6 | 74.4 | 73.5 | 0 | — | 5790–7560 | 6710 |
| 2,5-Hexanediol | 24 | 76 | 0 | 0 | — | 6540–10070 | 7720 |
| 1,6-Hexanediol | 34 | 66 | 73.5 | 0 | — | 7050–8820 | 7950 |
| 1,6-Hexanediol | 34 | 66 | 0 | 80 | — | 8560–9570 | 9120 |
| 1,6-Hexanediol | 7 | 93 | 0 | 0 | — | 7550–37010 | 16280 |

TABLE II-continued
STRENGTH PROPERTIES OF FILLED AND UNFILLED CYANOACRYLATE POLYMER COMPOSITIONS

| Difunctional Bis (2-Cyanoacrylate) of the Diol - | % Monomer Content Based On Total Weight Monomers Present In Composition | | Filler Content Based On Weight Total Composition | | Lap Shear Adhesion PSI | Breaking Strength PSI | |
|---|---|---|---|---|---|---|---|
| | Percent Difunctional Monomer | Percent Isobutyl-2-(Cyanoacrylate) | Alumina Filler % By Weight | Quartz Filler % By Weight | | Range | Average |
| 1,6-Hexanediol | 30 | 70 | 0 | 0 | 450 | 9810–12810 | 11460 |
| 1,6-Hexanediol | 34 | 66 | 0 | 0 | — | 6630–16790 | 10540 |
| 1,8-Octanediol | 17.6 | 82.4 | 73.5 | 0 | — | 6320–7070 | 6640 |
| 1,8-Octanediol | 17 | 83 | 0 | 0 | — | 5750–10200 | 8270 |
| 1,9-Nonanediol | 10 | 90 | 75 | 0 | 1700 | 7660–8460 | 8070 |
| 1,9-Nonanediol | 33 | 67 | 73.5 | 0 | — | 4480–7610 | 5880 |
| 1,9-Nonanediol | 8 | 92 | 0 | 0 | 1320 | 12340–21180 | 17760 |
| 1,9-Nonanediol | 30 | 70 | 0 | 0 | 620 | 13300–22880 | 16740 |
| 1,10-Decanediol | 7.5 | 92.5 | 73.5 | 0 | — | 5560–7330 | 6170 |
| 1,10-Decanediol | 7.5 | 92.5 | 0 | 80 | — | 6880–7370 | 7070 |
| 1,10-Decanediol | 7.5 | 92.5 | 0 | 0 | 880 | 5170–17460 | 10880 |
| 1,12-Dodecanediol | 6.7 | 93.3 | 73.5 | 0 | — | 5100–6390 | 5700 |
| 1,12-Dodecanediol | 6.5 | 93.5 | 0 | 0 | 1990 | 5100–7650 | 6850 |
| 1,3-bis (hydroxymethyl) tetramethyldisiloxane | 50 | 50 | 73.4 | 0 | — | 2980–5820 | 4170 |
| 1,3-bis (hydroxymethyl) tetramethyldisiloxane | 100 | 0 | 0 | 75 | — | 3400–5820 | 4610 |
| 1,3-bis (hydroxymethyl) tetramethyldisiloxane | 100 | 0 | 0 | 0 | 300 | 11790–21390 | >15870 |

From Table III it can be observed that upon aging in water at an elvated temperature (100°F), the breaking strength of polymerized comonomer blends improves. Incidentally, these are the conditions of temperature that prevail in warm blooded animals' mouth, making these compositions especially suitable for dental applications.

TABLE III

Effect of Aging Time at 100°F in Water on Breaking Strength
Monomer: Isobutyl-2-cyanoacrylate/Ethylene Glycol Bis (2-Cyanoacrylate) (EGBCA)
Filler: Alumina, 72% w

| Isobutyl-2-Cyanoacrylate/ EGBCA (w/w) Monomer Mix | Breaking Strength, psig (avg.) | |
|---|---|---|
| | 100°F/24 hrs. | 100°F/7 days |
| 100% IBC (Control) | 6350 | 6870 |
| 99/1 | 6520 | 8140 |
| 98/2 | 6380 | 7790 |
| 96/4 | 7360 | 8700 |
| 94/6 | 7600 | 9300 |
| 90/10 | 8160 | — |
| 80/20 | 8380 | — |

Furthermore, it can be seen from Table IV that this increase in breaking strength is not limited to polymerized comonomer blends of the monomers of this invention and isobutyl-2-cyanoacrylate, but extends to esters of 2-cyanoacrylic acid generally.

TABLE IV

Effect of the Alkyl Group in Alkyl 2-Cyanoacrylate Monomers on Breaking Strengths of Crosslinked Alumina Filled Composites Crosslinking monomer: Ethylene Glycol Bis (2-Cyanoacrylate) (EGBCA)
Filler: 72% w Alumina

| Alkyl Group of 2-Cyanoacrylate Monomer | Breaking Strengths, psi | |
|---|---|---|
| | Alkyl Cyanoacrylate alone | Cyanoacrylate + 3.6 mole % EGBCA |
| Ethyl | 7290 | 6060 |
| Isobutyl | 5470 | 7180 |
| n-Amyl | 2160 | 3070 |
| i-Amyl | 4590 | 5060 |
| n-Hexyl | 980 | 1450 |
| n-Heptyl | 390 | 670 |

EXAMPLE XXVI

Improvement in resistance to moisture of cyanoacrylate bonds through the inclusion of small amounts of biscyanoacrylate monomer in the monomer mix used is illustrated.

Steel plates, ½ × 2 × 0.1 inches were freed of rust and cleaned by successive immersion in dilute hydrochloric acid, water, dilute ammonium hydroxide, water, and acetone.

Bonding was effected by addition of a small drop of cyanoacrylate monomer on the end of one plate, followed by careful placement of the other plate to give a ½ × ½ inch lap joint. A 37.5 gram weight was placed on the lap joint until adhesive bonding took place. A set of 10 specimens was prepared for shear adhesion testing under the conditions shown in the accompanying Table. The abbreviation 100°F/H$_2$O/1 day indicates, for instance, that the specimen was kept immersed in water at 100°F. for 1 day prior to the shear test.

The IBC (isobutyl 2-cyanoacrylate) monomer formulations were all catalyzed with a trace amount of N,N-dimethyl-p-toluidine catalyst in order to effect an adhesive bond within two minutes. The MCA (methyl cyanoacrylate), a commercial adhesive (Loctite* Quick-Set Adhesive 404; Loctite Corp.), and its blend with the crosslinking monomer, 1,8-octanediol bis(2-cyanoacrylate), formed an almost instantaneous bond and did not require addition of a catalyst.

All crosslinkable cyanoacrylate formulations were based on a 90% alkyl 2-cyanoacrylate and a 10% w 1,8-octanediol bis(2-cyanoacrylate) (1,8-ODBCA) blend.

Shear adhesion testing was done on an Instron tester at a pull-rate of 0.5 inches/minute. The values shown in the Table are averages of 10 specimen measurements.

Based on the tabulated data, the following conclusions can be reached.

While MCA gave higher initial bond strengths than the IBC, the shear adhesive bond strength of the former deteriorated to about 30% of the initial bond strength after 7 days in water at 100°F. The IBC and the crosslinked IBC bonded specimens were not affected under the same conditions. The crosslinked IBC bond strength was at least 20% greater than that obtained with IBC alone. Incorporation of the crosslinking monomer into MCA did not appear to improve the initial bond strength but gave an adhesive bond which was much more resistant to degradation in water, comparing for example the 7 day drop from 2612 to 780 psi for MCA vs the 2000 to 1156 psi for the crosslinked MCA. After 7 days in water, the crosslinked MCA bond strength (1156 psi) was about 48% greater than that of the non-crosslinked MCA (780 psi).

TABLE

SHEAR ADHESIVE BOND STRENGTHS OF CROSSLINKED VS NON-CROSSLINKED IBC AND MCA
Shear Adhesive Bond Strength, in psi

| Conditioned at | IBC | 90/10 IBC/1,8-ODBCA | MCA | 90/10 MCA/1,8-ODBCA |
|---|---|---|---|---|
| 100°F/air/1 day | 508 | 612 | 2612 | 2000 |
| 100°F/H₂O/1 day | 512 | 812 | 1660 | 1476 |
| 100°F/H₂O/7 days | 524 | 628 | 780 | 1156 |

From the foregoing description, it is apparent that the objects of this invention have been achieved in a new and novel manner. While only specific embodiments have been illustrated, it should be apparent from the foregoing description to those skilled in the art that other alternatives can be practiced within the spirit and the scope of the present invention.

What is claimed is:

1. In the preparation of bis (2-cyanoacrylate) monomer represented by the General Formula VI

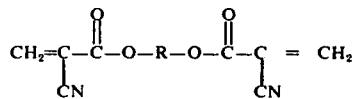

from 2-cyanoacrylic acid ester of the General Formula I

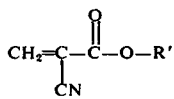

the steps comprising:

a. introducing a blocking group $\text{\textcircled{D}}$ by means of a Diels-Alder reaction in which a cyclic 1,3-diene is reacted with said cyanoacrylic ester of Formula I to give a compound of the General Formula II

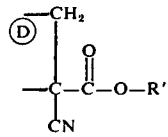

b. converting said compound of General Formula II by hydrolysis to a compound represented by Formula III

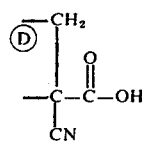

converting the compound of Formula III to an acyl halide represented by the General Formula IV(B):

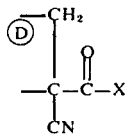

c. coupling two acyl groups of compounds of Formula IV(B) to each other through an — O — R — O — linkage by esterification with a difunctional alcohol to form a compound represented by the General Formula V

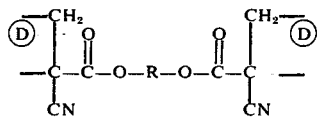

d. and then heating the compound of Formula V with maleic anhydride to displace said blocking groups and form said bis (2-cyanoacrylate) of Formula VI; wherein said blocking group

of Formula II, III, and V is any one of the group consisting of

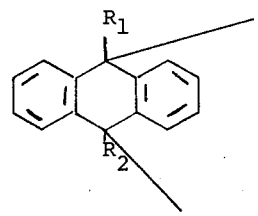

where $R_1$ and $R_2$ are the same $R_1$ and $R_2$ are selected from the group consisting of H, an alkyl group of 1 to 5 carbons, phenyl, Br or Cl and where $R_1$ and $R_2$ are different, $R_1$ is H and $R_2$ is a member selected from any of the group consisting of an alkyl group of 1 to 5 carbons, phenyl, Br and Cl;

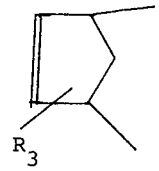

where $R_3$ is H or $CH_3$; and

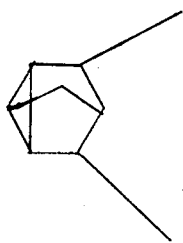

wherein the organo linking group R of Formulas VI and V is the same and is any one of the group consisting of:

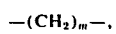

where $m$ is an integer of from 1 to 20 inclusive;

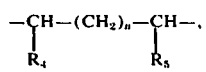

where $n$ is an integer of from 0 to 18 inclusive, and $R_4$ and $R_5$ are independently hydrogen or a $C_1$ to $C_5$ alkyl group, $R_4$ and $R_5$ not simultaneously being hydrogen;

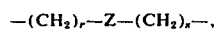

where Z is —O—, —S—, —CH=CH—; —C≡C—;

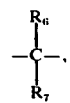

and

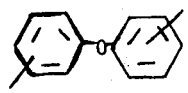

where $r$ and $s$ are independent integers of from 1 to 10 inclusive and $r$ and $s$ total from 2 to 20, $R_6$ and $R_7$ are independently hydrogen or a straight or branched chain $C_1$ and $C_5$ alkyl group

where $x$ and $y$ are integers of from 1 to 6 inclusive;

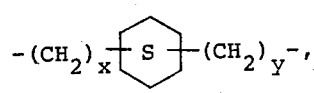

where $x$ and $y$ are as hereinbefore defined;

—$CH_2$—$(CF_2)_z$—$CH_2$—, where $z$ is an integer of from 1 to 10 inclusive; and

and wherein R' of Formula I and II is an alcohol moiety selected from $C_1$ to $C_{16}$ alkyl, cyclohexyl or phenyl.

2. A method according to claim 1 in which the cyclic 1,3 diene is selected from the group consisting of anthracene, 9-methylanthracene, 9-bromoanthracene, 9-phenylanthracene, 9,10-dimethylanthracene, 9,10-dibromoanthracene, 9,10-diphenylanthracene, cyclopentadiene, methylcyclopentadiene, and norbornadiene.

3. A method according to claim 2 in which the diene is cyclopentadiene.

4. A method according to claim 1 where the difunctional alcohol is of the formula HO(R'')$_t$OH where when $t$ is = to or > 1, R'' is propylene, and when $t$ is > 2, R'' is propylene, tetramethylene and ethylene, and $t$ is a range average such that the molecular weight is from about 76 to about 2000.

5. A method according to claim 1 wherein from 25 to 200 mole percent excess of maleic anhydride is employed.

6. A method according to claim 1 where the cyanoacrylic ester is isobutyl 2-cyanoacrylate.

7. A method according to claim 1 in which the diene is anthracene.

8. A method according to claim 1 wherein the glycol is HO—$(CH_2)_m$—OH, where $m$ is an integer of from 1 to 20 inclusive.

9. A method according to claim 1 in which the difunctional alcohol is selected from the group consisting of HO—$(CH_2)_m$—OH where $m$ is an integer of from 1 to 20 inclusive;

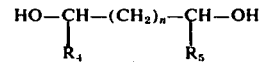

where $n$ is an integer of from 0 to 18 and $R_4$ and $R_5$ are independently selected from the group consisting of hydrogen and $C_1$ to $C_5$ alkyl, but $R_4$, and $R_5$ not simultaneously being hydrogen;

HO—$(CH_2)_r$—Z—$(CH_2)_s$—OH where Z is —O—, —S—, —CH=CH—, —C≡C—,

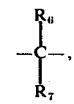

and

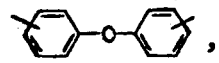

where $r$ and $s$ are independent integers of from 1 to 10 inclusive and $r$ and $s$ total from 2 to 20, $R_6$ and $R_7$ being as heretofore defined;

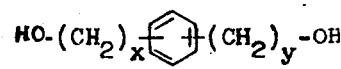

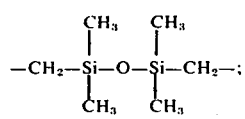

where x and y are integers of from 1 to 6 inclusive;

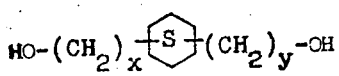

where x and y are as hereinbefore defined;
HO—CH$_2$—(CF$_2$)$_z$—CH$_2$—OH where z is an integer of from 1 to 10 inclusive; and
HO—CH$_2$—Si(CH$_3$)$_2$—O—Si(CH$_3$)$_2$—CH$_2$—OH.

10. In the preparation of bis (2-cyanoacrylate) monomer represented by the General Formula VI

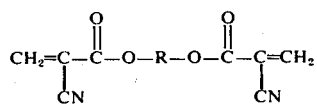

from 2-cyanoacrylic acid ester of the General Formula I

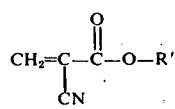

the steps comprising:
a. introducing a blocking group Ⓓ by means of a Diels-Alder reaction in which a cyclic 1,3-diene is reacted with said cyanoacrylic ester of Formula I to give a compound of the General Formula II

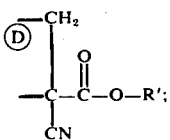

b. converting said compound of General Formula II by hydrolysis to a compound represented by Formula III

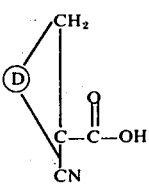

neutralizing the compound of Formula III with a metal base of which the designation M is the metal to form a metal salt compound of the General Formula IV(A):

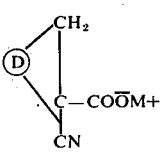

c. coupling two carboxyl groups of compounds of Formula IV(A) to each other through an organo-linking group - R - by ester formation through reac-tion with a dihalide to form a compound represented by the General Formula V

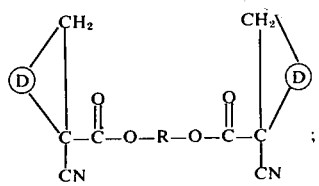

and then heating the compound of Formula V with maleic anhydride to displace said blocking groups and form said bis (2-cyanoacrylate) of Formula VI; wherein said blocking group

of Formula II, III, IV(A) and V is any one of the group consisting of

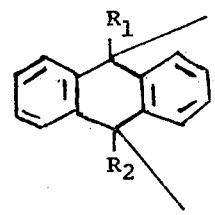

where R$_1$ and R$_2$ are the same, R$_1$ and R$_2$ are selected from the group consisting of H, an alkyl group of 1 to 5 carbons, phenyl, Br or Cl and where R$_1$ and R$_2$ are different, R$_1$ is H and R$_2$ is a member selected from any of the group consisting of an alkyl group of 1 to 5 carbons, phenyl, Br and Cl;

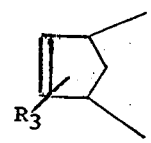

where R$_3$ is H or CH$_3$; and

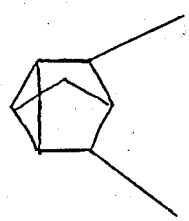

wherein the organo linking group R of Formulas VI and V is the same and is any one of the group consisting of:

where m is an integer of from 1 to 20 inclusive;

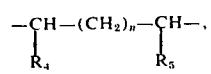

where $n$ is an integer of from 0 to 18 inclusive, and $R_4$ and $R_5$ are independently hydrogen or a $C_1$ to $C_5$ alkyl group, $R_4$ and $R_5$ not simultaneously being hydrogen;

$$-(CH_2)_r-Z-(CH_2)_s-,$$

where Z is $-O-$, $-S-$, $-CH=CH-$; $-C\equiv C-$;

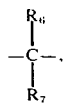

and

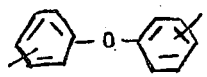

where $r$ and $s$ are independent integers of from 1 to 10 inclusive and $r$ and $s$ total from 2 to 20, $R_6$ and $R_7$ are independently hydrogen or a straight or branched chain $C_1$ to $C_5$ alkyl group

where $x$ and $y$ are integers of from 1 to 6 inclusive;

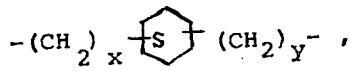

where $x$ and $y$ are as hereinbefore defined;

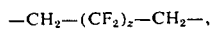

where $z$ is an integer of from 1 to 10 inclusive; and

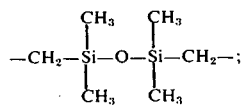

and wherein R' of Formula I and II is an alcohol moiety selected from $C_1$ to $C_{16}$ alkyl, cyclohexyl or phenyl.

11. A method according to claim 10 in which the dihalide is selected from the group consisting of $X-(CH_2)_m-X$, where $m$ is an integer of from 1 to 20 inclusive;

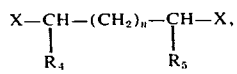

where $n$ is an integer of from 0 to 18 and $R_4$ and $R_5$ are independently selected from the group consisting of hydrogen and $C_1$ to $C_5$ alkyl, but $R_4$ and $R_5$ not simultaneously being hydrogen;

$X-(CH_2)_r-Z-(CH_2)_s-X$, where Z is $-O-$, $-S-$, $-CH=CH-$, $-C\equiv C-$,

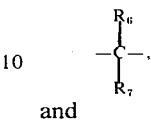

and

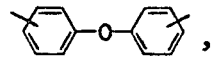

where $r$ and $s$ are independent integers of from 1 to 10 inclusive and $r$ and $s$ total from 2 to 20, $R_6$ and $R_7$ are independently hydrogen or a straight or branched chain $C_1$ to $C_5$ alkyl group

where $x$ and $y$ are integers of from 1 to 6 inclusive;

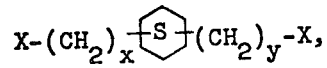

where $x$ and $y$ are as hereinbefore defined;
$X-CH_2-(CF_2)_z-CH_2-X$, where $z$ is an integer of from 1 to 10 inclusive; and
$X-CH_2-Si(CH_3)_2-O-Si(CH_3)_2-CH_2-X$; and
X is either independently selected from the halogens chlorine, bromine, and iodine.

12. A method according to claim 11 wherein the dihalide is $X-(CH_2)_m-X$, where $m$ is an integer of from 1 to 20 inclusive.

13. A method according to claim 10 in which the cyclic 1,3 diene is selected from the group consisting of anthracene, 9-methylanthracene, 9-bromoanthracene, 9-phenylanthracene, 9,10-dimethylanthracene, 9,10-dibromoanthracene, 9,10-diphenylanthracene, cyclopentadiene, methylcyclopentadiene, and norbornadiene.

14. A method according to claim 13 in which the diene is cyclopentadiene.

15. A method according to claim 10 wherein from 25 to 200 mole percent excess of maleic anhydride is employed.

16. A method according to claim 10 where the cyanoacrylic ester is isobutyl 2-cyanoacrylate.

17. A method according to claim 10 in which the diene is anthracene.

* * * * *